(12) United States Patent
Yager

(10) Patent No.: US 9,103,803 B2
(45) Date of Patent: Aug. 11, 2015

(54) DEFECT DETECTION IN SATURABLE ABSORBERS

(71) Applicant: Empire Technology Development LLC, Wilmington, DE (US)

(72) Inventor: Thomas A. Yager, Encinitas, CA (US)

(73) Assignee: Empire Technology Development LLC, Wilmington, DE (US)

( * ) Notice: Subject to any disclaimer, the term of this patent is extended or adjusted under 35 U.S.C. 154(b) by 157 days.

(21) Appl. No.: 13/825,492

(22) PCT Filed: Oct. 10, 2012

(86) PCT No.: PCT/US2012/059599
§ 371 (c)(1),
(2) Date: Mar. 21, 2013

(87) PCT Pub. No.: WO2014/058422
PCT Pub. Date: Apr. 17, 2014

(65) Prior Publication Data
US 2014/0285796 A1    Sep. 25, 2014

(51) Int. Cl.
*G01N 21/00* (2006.01)
*G01N 21/95* (2006.01)
(Continued)

(52) U.S. Cl.
CPC ............ *G01N 21/95* (2013.01); *G01N 21/8422* (2013.01); *H01L 29/1606* (2013.01); *G01N 21/9501* (2013.01)

(58) Field of Classification Search
CPC .......... G01N 21/9501; G01N 21/8806; G01N 21/94; G01N 21/956; G01N 21/88
USPC ...................................................... 356/237.1
See application file for complete search history.

(56) References Cited

U.S. PATENT DOCUMENTS

| 4,310,250 A | 1/1982 | Sick et al. |
| 4,310,520 A | 1/1982 | Sick et al. |
| 7,760,364 B1 | 7/2010 | Zhuang et al. |

(Continued)

FOREIGN PATENT DOCUMENTS

KR    20120094708 A    8/2012

OTHER PUBLICATIONS

Nolen, "Large-Scale Automated Identification and Quality Control of Exfoliated and CVD Graphene via Image Processing Technique. "ECS Transactions—Las Vegas, NV" vol. 33, " State-of-the-Art Program on Compound Semiconductors 52 (SOTAPOCS 52), 218th Electrochemical Society (ECS) Meeting, Oct. 10-15, 2010.

(Continued)

*Primary Examiner* — Tarifur Chowdhury
*Assistant Examiner* — Md Rahman
(74) *Attorney, Agent, or Firm* — Turk IP Law, LLC

(57) ABSTRACT

Technologies are generally described for identifying defects in saturable absorbers, such as graphene, by the saturable property of decreasing light absorbance with increasing light intensity. For example, a graphene coated substrate may be imaged twice under two distinct incident intensities. At a gap in the graphene, the substrate may reflect light proportional to the incident intensities. The graphene may show a non-linear increase in reflected light as the intensity of illumination increases. A difference between the two incident intensities may reveal the gap in the graphene. Any suitable imaging technique may be employed such as confocal microscopy or linear scanning. The imaging may be scaled up for high volume automated inspection.

27 Claims, 13 Drawing Sheets

(51) Int. Cl.
*H01L 29/16* (2006.01)
*G01N 21/84* (2006.01)

(56) References Cited

U.S. PATENT DOCUMENTS

| | | | |
|---|---|---|---|
| 2001/0000279 A1* | 4/2001 | Daniels et al. | 73/105 |
| 2005/0249667 A1* | 11/2005 | Tuszynski et al. | 424/9.3 |
| 2007/0187606 A1* | 8/2007 | Adel et al. | 250/341.1 |
| 2008/0129988 A1 | 6/2008 | Saito et al. | |
| 2009/0023853 A1 | 1/2009 | Tsukada et al. | |

OTHER PUBLICATIONS

Bao et, al., "Monolayer Graphene as a Saturable Absorber in a Mode-Locked Laser", Nano Res. 2011, 4(3): 297-307.
"Saturable absorption", Retrieved at <<http://en.wikipedia.org/wiki/Saturable_absorption>>, Last modified on Mar. 14, 2013, p. 1.
International Search Report and Written Opinion for PCT/US2012/59599 dated Jan. 2, 2013.

* cited by examiner

DEFECT DETECTION IN SATURABLE ABSORBERS

CROSS-REFERENCE TO RELATED APPLICATION

This Application is the National Stage filing under 35 U.S.C. §371 of PCT Application Ser. No. PCT/US2012/059599 filed on Oct. 10, 2012.

BACKGROUND

Unless otherwise indicated herein, the materials described in this section are not prior art to the claims in this application and are not admitted to be prior art by inclusion in this section.

Single and multilayer graphene films are of much current interest in electrical circuits, displays, and other fields. Many applications, such as electronics, may benefit from continuous portions of graphene with predictable conductivity, for example. Chemical vapor deposition (CVD), a common method of preparing graphene, may include growth of a graphene film on a transition metal substrate followed by transfer to a second substrate. Such processes of growth and transfer may produce macro-crack and void defects that may be difficult to detect without specialized laboratory tools, such as Raman Spectroscopy. Identification of such defects is of interest for process control and quality assurance of systems that may include graphene. However, specialized tools such as Raman Spectroscopy may be undesirably slow for scanning large areas of graphene, particularly in production scale environments.

The present disclosure appreciates that quickly identifying cracks and voids in graphene films may be a complex undertaking.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

The present disclosure generally describes methods, apparatus, and computer program products for imaging one or more defects in saturable absorbers, for example, graphene.

Some examples embodiments may include various methods of imaging one or more defects in a saturable absorber. Example methods may include acquiring a first reflected intensity of a saturable absorber for a location on the saturable absorber under bright field electromagnetic radiation at a first incident intensity, and acquiring a second reflected intensity of the saturable absorber for the location under bright field electromagnetic radiation at a second incident intensity. The second incident intensity may be greater than the first incident intensity by an amount sufficient to at least partly saturate an absorbance value of the saturable absorber. The example methods may also include determining an incident intensity ratio corresponding to the second incident intensity divided by the first incident intensity; determining a reflected intensity ratio for the location corresponding to the second reflected intensity divided by the first reflected intensity; generating a reflected intensity ratio map for the saturable absorber by determining reflected intensity ratios for a plurality of locations on the saturable absorber; and comparing the reflected intensity ratio to the incident intensity ratio to identify one or more defects at one or more of the plurality of locations.

Further example embodiments may include a computer-readable storage medium having machine executable instructions stored thereon for detecting defects in a saturable absorber. The computer readable storage media may include machine executable instructions to control an illumination source to selectively direct bright field electromagnetic radiation at a first incident intensity to a location on the saturable absorber at the sample stage. Instructions may be included to control an imaging device to acquire a first reflected intensity of the saturable absorber for the location under bright field electromagnetic radiation at the first incident intensity. Instructions may also be included to control the illumination source to selectively direct bright field electromagnetic radiation at a second incident intensity to the location on the saturable absorber. The second incident intensity may be greater than the first incident intensity by an amount sufficient to at least partly saturate an absorbance value of the saturable absorber. Instructions may be included to control the imaging device to acquire a second reflected intensity of the saturable absorber for the location under bright field electromagnetic radiation at the second incident intensity. Instructions may further be included to determine an incident intensity ratio corresponding to the second incident intensity divided by the first incident intensity. Instructions may be included to determine a reflected intensity ratio for the location corresponding to the second reflected intensity divided by the first reflected intensity. Instructions may also be included to generate a reflected intensity ratio map for the saturable absorber by determining reflected intensity ratios for a plurality of locations on the saturable absorber. The reflected intensity ratio map may be an image of one or more defects in the saturable absorber. Instructions may further be included to compare the reflected intensity ratio to the incident intensity ratio to identify one or more defects at one or more of the plurality of locations. Instructions may be included to identify an absence of defects at a location on the saturable absorber where the reflected intensity ratio may be greater than the incident intensity ratio.

Yet other example embodiments may include systems for detecting defects in a saturable absorber. Example systems may include a sample stage configured to hold a sample; an illumination source configured to selectively illuminate the sample stage under direct bright field and dark field electromagnetic radiation of selectable intensity; an imaging device configured to selectively acquire bright field reflected intensities and dark field reflected intensities of the sample; and a microprocessor coupled to the sample stage, the illumination source, and the imaging device. The microprocessor may be configured via machine executable instructions. Instructions may be included to control an illumination source to selectively direct bright field electromagnetic radiation at a first incident intensity to a location on the saturable absorber at the sample stage. Instructions may be included to control an imaging device to acquire a first reflected intensity of the saturable absorber for the location under bright field electromagnetic radiation at the first incident intensity. Instructions may also be included to control the illumination source to selectively direct bright field electromagnetic radiation at a second incident intensity to the location on the saturable absorber. The second incident intensity may be greater than the first incident intensity by an amount sufficient to at least partly saturate an absorbance value of the saturable absorber. Instructions may be included to control the imaging device to acquire a second reflected intensity of the saturable absorber for the location under bright field electromagnetic radiation at the second incident intensity. Instructions may further be included to determine an incident intensity ratio corresponding to the second incident intensity divided by the first incident intensity. Instructions may be included to determine a reflected intensity ratio for the location corresponding to the second reflected intensity divided by the first reflected intensity. Instructions may also be included to generate a reflected intensity ratio map for the saturable absorber by determining reflected intensity ratios for a plurality of locations on the saturable absorber. The reflected intensity ratio map may be an image of one or more defects in the saturable absorber. Instructions may further be included to compare the reflected intensity ratio to the incident intensity ratio to identify one or more defects at one or more of the plurality of locations. Instructions may be included to identify an absence of defects at a location on the saturable absorber where the reflected intensity ratio may be greater than the incident intensity ratio.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

Figure 1:
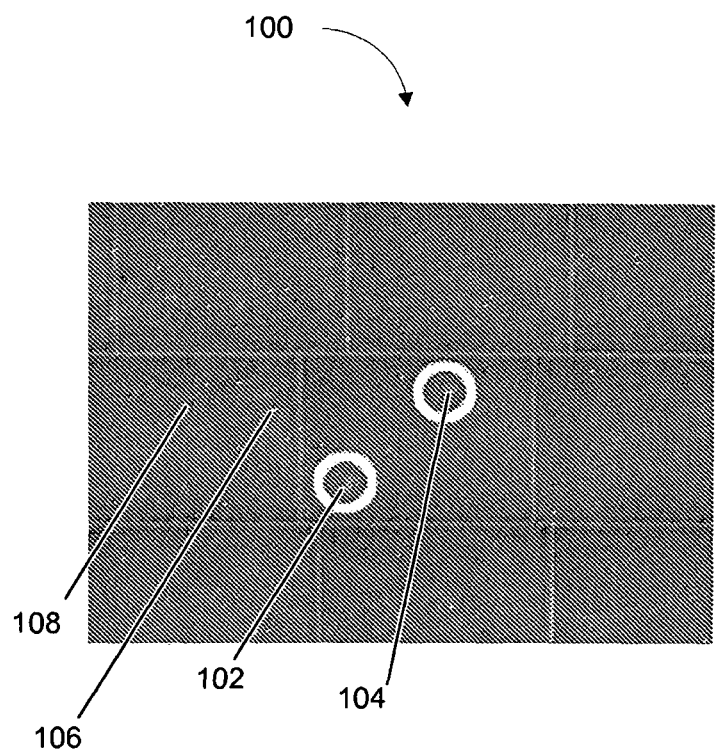
FIG. 1 is a representative tiled photomicrograph of a silicon wafer coated with single layer CVD graphene, showing various defects in the graphene.

all arranged in accordance with at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, devices, and/or computer program products related to detecting defects in saturable absorbers.

Briefly stated, defects in saturable absorbers, such as graphene, may be identified by the saturable property of decreasing light absorbance with increasing light intensity. For example, a graphene coated substrate may be imaged twice under two distinct incident intensities. At a gap in the graphene, the substrate may reflect light proportional to the incident intensities. The graphene may show a non-linear increase in reflected light as the intensity of illumination increases. A difference between the images at the two incident intensities may reveal the gap in the graphene. Any suitable imaging technique may be employed such as confocal microscopy or linear scanning. The imaging may be scaled up for high volume automated inspection.

As used herein, "saturable absorbance" may refer to a property of materials, where the absorbance of electromagnetic radiation by the material decreases with increasing intensity of the electromagnetic radiation. At sufficiently high incident intensity of the electromagnetic radiation, electrons in the ground state of a saturable absorber material may become excited into an upper energy state. The excitation may occur at such a rate that there may be insufficient time for the atoms to decay back to the ground state before the ground state becomes depleted, and the absorbance may then saturate. Since graphene is only one atom thick, there are fewer electrons in the ground state become depleted when exposed to sufficient intensity of electromagnetic radiation. Linear optical absorption occurs under low excitation intensity, where electrons from the valence band are excited into the conduction band forming electron-hole pairs. Here, electron-hole recombination dominate the process until the equilibrium electron and hole distribution is restored. Saturable absorption occurs as the excitation is increased to higher intensity, causing the photogenerated carriers to increase in concentration. The states near the edge of the conduction and valence bands fill, blocking further absorption, and thus imparting transparency to light at photon energies just above the band edge.

As used herein, saturable absorbance as a function of intensity [α*(I)] may be mathematically represented by to Equation (1):

$$\alpha^*(I) = \frac{\alpha_S^*}{1 + \frac{I}{I_S}} + \alpha_{NS}^* \quad (1)$$

In Equation (1): $\alpha_S^*$ may represent the saturable component of absorbance; $\alpha_{NS}^*$ may represent the non-saturable component of absorbance; I may represent the incident intensity; and $I_S$ may represent the saturable intensity.

As used herein, a "saturable absorber" may be a material that displays saturable absorbance. Most materials show some saturable absorption, but often only at very high optical intensities resulting in optical damage to the material. Semiconductor materials have been used as saturable absorbers and in include III-V semiconductors (e.g., GaAs, InP, etc), nano materials such as carbon nanotubes (often dispersed in a polymer) and graphene. Since the photonic response of graphene has been reported to be universal and wavelength independent, a graphene saturable absorber may be regarded as a full-band optical element ranging from the ultraviolet through the infrared and even into the Terahertz range of the electromagnetic spectrum.

FIG. 1 is a representative tiled photomicrograph of a silicon wafer coated with single layer CVD graphene 100, showing various defects in the graphene, in accordance with at least some aspects described herein. FIG. 1 represents a composite image of several individual image tiles that have been stitched together. The circled regions illustrate examples of void regions 102 and 104 in single layer CVD graphene 100. Other light colored objects such as 106 and 108 may represent other voids, debris on top of the graphene, or debris below the graphene. It may be difficult to reliably distinguish or identify features (102, 104, 106, and 108) as voids, debris on top of the graphene, or debris below the graphene by photographic methods.

Figure 2:
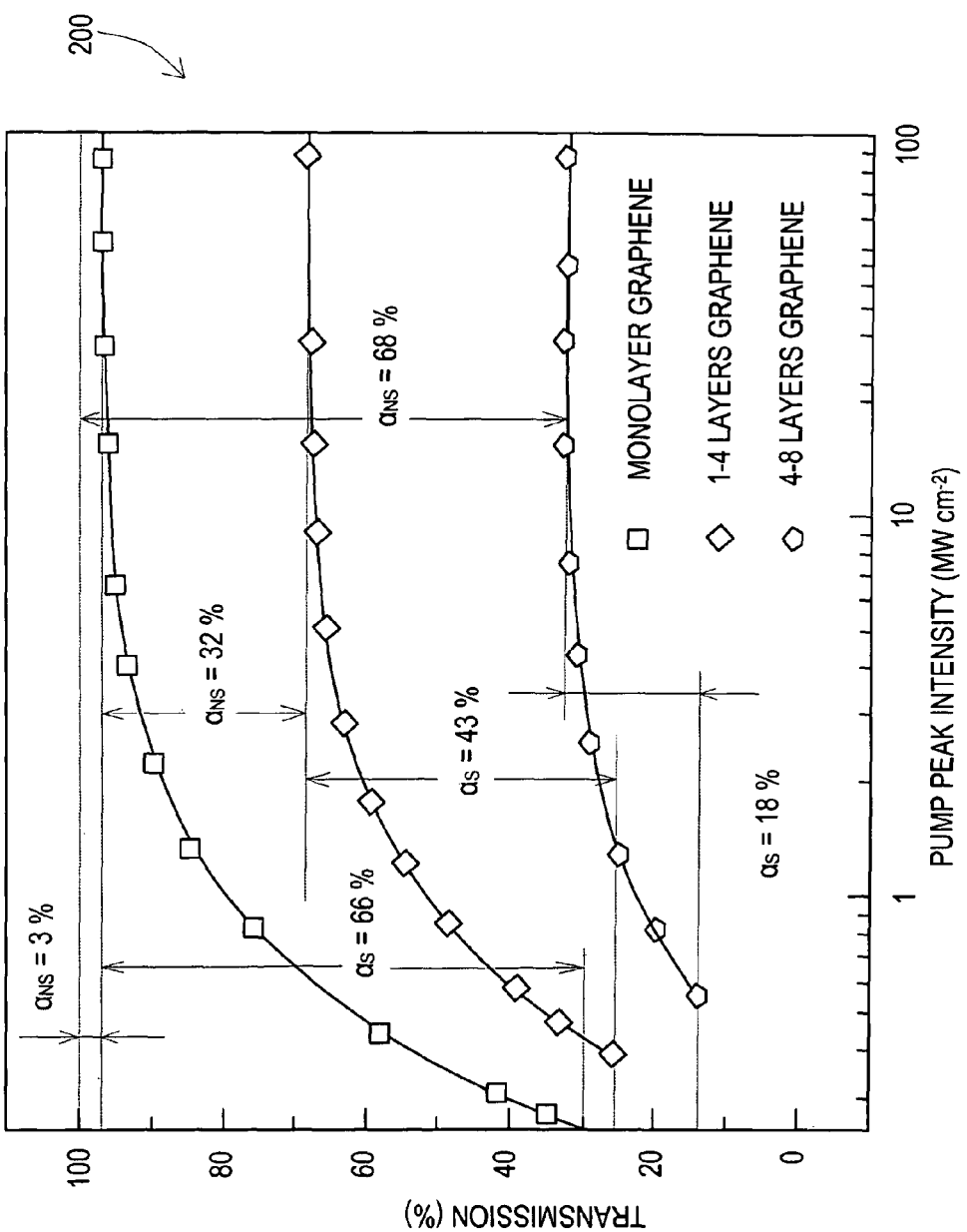
FIG. 2 is a representative plot of percent transmission versus pump peak intensity in a saturable absorber.

FIG. 2 is a representative plot of percent transmission versus pump peak intensity in a saturable absorber, graphene, in accordance with at least some aspects described herein. This data was experimentally determined (Monolayer Graphene as a Saturable Absorber in a Mode-Locked Laser—Q. Bao et. al., Nano Res. 2011, 4(3): 297-307). These power-dependent nonlinear absorption measurements used a soliton mode locked fiber laser working at 1550 nm with an output pulse width of ~1 ps and repetition rate of ~5 MHz as input seed pulse. The measurements varied the input power from ~−40 dBm (i.e., 100 nW)-14 dBm. The data in FIG. 2 show that saturable absorbance may decrease with increasing layers of graphene, from a monolayer, to few-layer graphene of about 1-4 layers, to multilayer graphene of about 4-8 layers.

FIG. 2 shows various example values of the saturable component of absorbance, represented by $\alpha_S^*$, and the non-saturable component of absorbance, represented by $\alpha_{NS}^*$, for a variety of configurations, including monolayer graphene ($\alpha_S^*$=65.9% and $\alpha_{NS}^*$=3.2%); few layer graphene of about 1-4 layers ($\alpha_S^*$=42.7% and $\alpha_{NS}^*$=31.5%); and multilayer graphene of about 4-8 layers ($\alpha_S^*$=18.2% and $\alpha_{NS}^*$=67.9%). These values may indicate that a monolayer may produce a greater modulation depth/contrast enhancement compared to few layer graphene of about 1-4 layers, and few layer graphene of about 1-4 layers may produce a greater modulation depth/contrast enhancement compared to multilayer graphene of about 4-8 layers. The curves in FIG. 2 were obtained using a 1550 nanometer pulsed laser with the following parameters: 1 picosecond pulse width; 5 Megahertz repeat rate; peak power level of 1 Megawatt per square centimeter; and a continuous average power level of about 5 Watts per square centimeter.

Figure 3A:
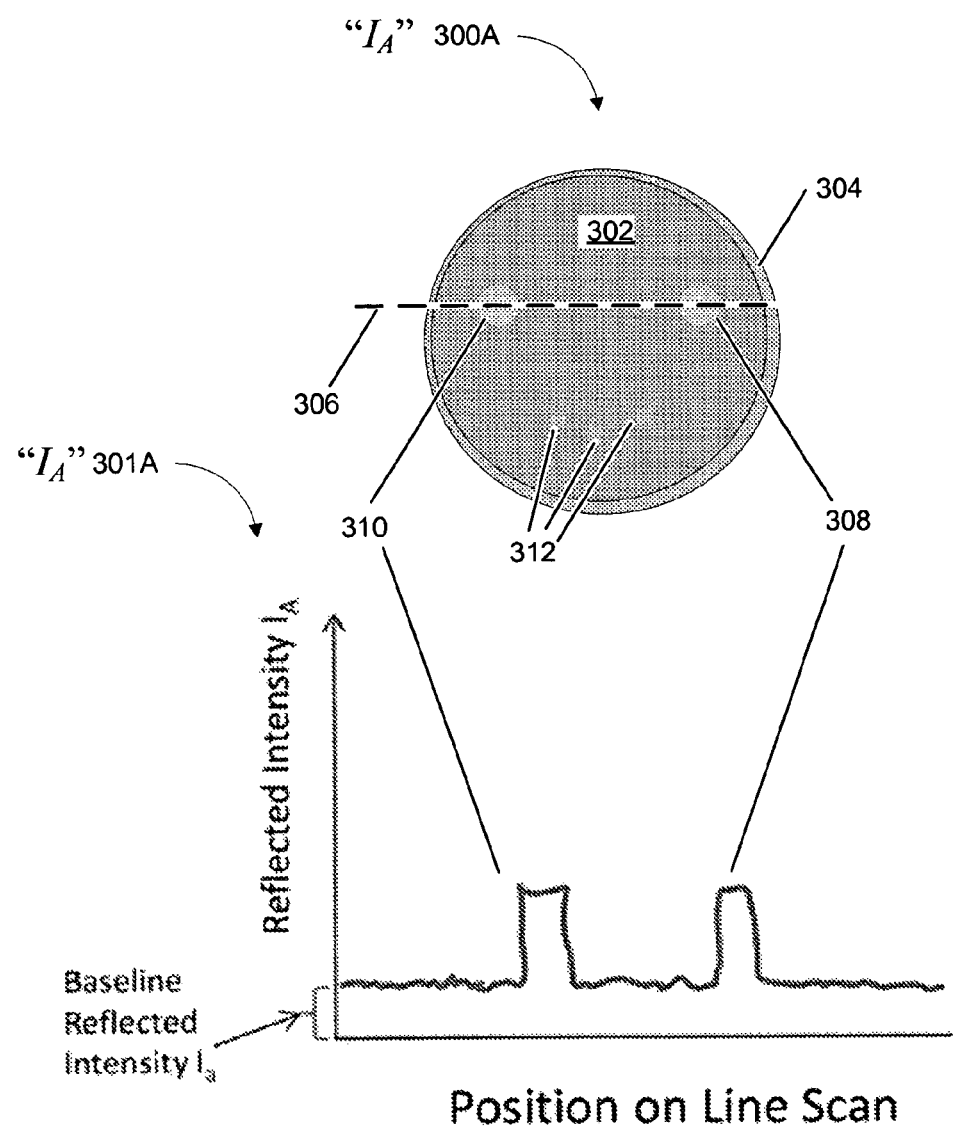
FIG. 3A shows a representative first reflected intensity image and a corresponding plot for a graphene sheet supported on a substrate.

FIG. 3A shows a representative first reflected intensity image and a corresponding plot for a graphene sheet supported on a substrate, arranged in accordance with at least some embodiments described herein. The representative first reflected intensity image 300A in FIG. 3A is of graphene 302 sheet supported on a substrate 304, with a corresponding plot 301A. A first reflected intensity image may be obtained under bright field electromagnetic radiation at a first incident intensity, for example, about 2.5 Watts per square centimeter as in 300A. In a plot for a first intensity image, such as plot 301A, the vertical axis may correspond to reflected intensity $I_A$ from the first incident intensity. The horizontal axis may correspond to the horizontal position on a reflected intensity image such as 300A, for example along axis 306. Plot 301A shows peaks in the reflected intensity $I_A$ along axis 306 corresponding to areas of higher reflected intensity 308 and 310.

For the purpose of determining defects in graphene, it may be desirable to identify gaps in graphene and to distinguish such gaps in graphene from substrate defects and/or surface debris. For the purpose of determining defects in substrates using a graphene layer as an imaging aid, it may be desirable to identify substrate defects and to distinguish such substrate defects from gaps in graphene and/or surface debris. In various examples, reflected intensity images such as 300A may show areas of higher reflected intensity, such as 308, 310, and 312 which may be attributed to various causes. For example, area 308 may represent a gap in graphene 302. Area 310 may appear superficially similar to area 308, but may represent a lighter spot on substrate 304 that shows through graphene 302 rather than a gap in graphene 302. Areas 312 may appear superficially similar to area 308, but may represent debris on top of graphene 302 rather than a gap in graphene 302.

As used herein, "bright field" may refer to imaging a sample where an illumination source and a detector are placed on the same or substantially the same axis, or on corresponding illumination and reflection axes with respect to reflection at a sample. Under "bright field" illumination, the detector may image a direct or substantially direct reflection of the sample.

As used herein, "dark field" may refer to imaging a sample where an illumination source and a detector are placed off-axis with respect to each other, or the detector may be located off of a reflection axis corresponding to the axis of the illumination source. Under "dark field" illumination, the detector may avoid imaging direct reflection of the sample. Rather, under "dark field" illumination, the detector may image scattered or diffused light from the sample, for example, as might be scattered or diffused by debris on the surface of a reflecting sample.

As used herein, the term "baseline reflected intensity" corresponds to the reflected intensity in an image of a region of unblemished graphene saturable absorber. For example, the baseline reflected intensity $I_\alpha$ may represent a reflected intensity corresponding to portions of reflected intensity image, such as 300A, other than defects, such as areas 308, 310, and 312. The baseline reflected intensity may be an average, a mean, a median, or another representative aggregate or average value.

Figure 3B:
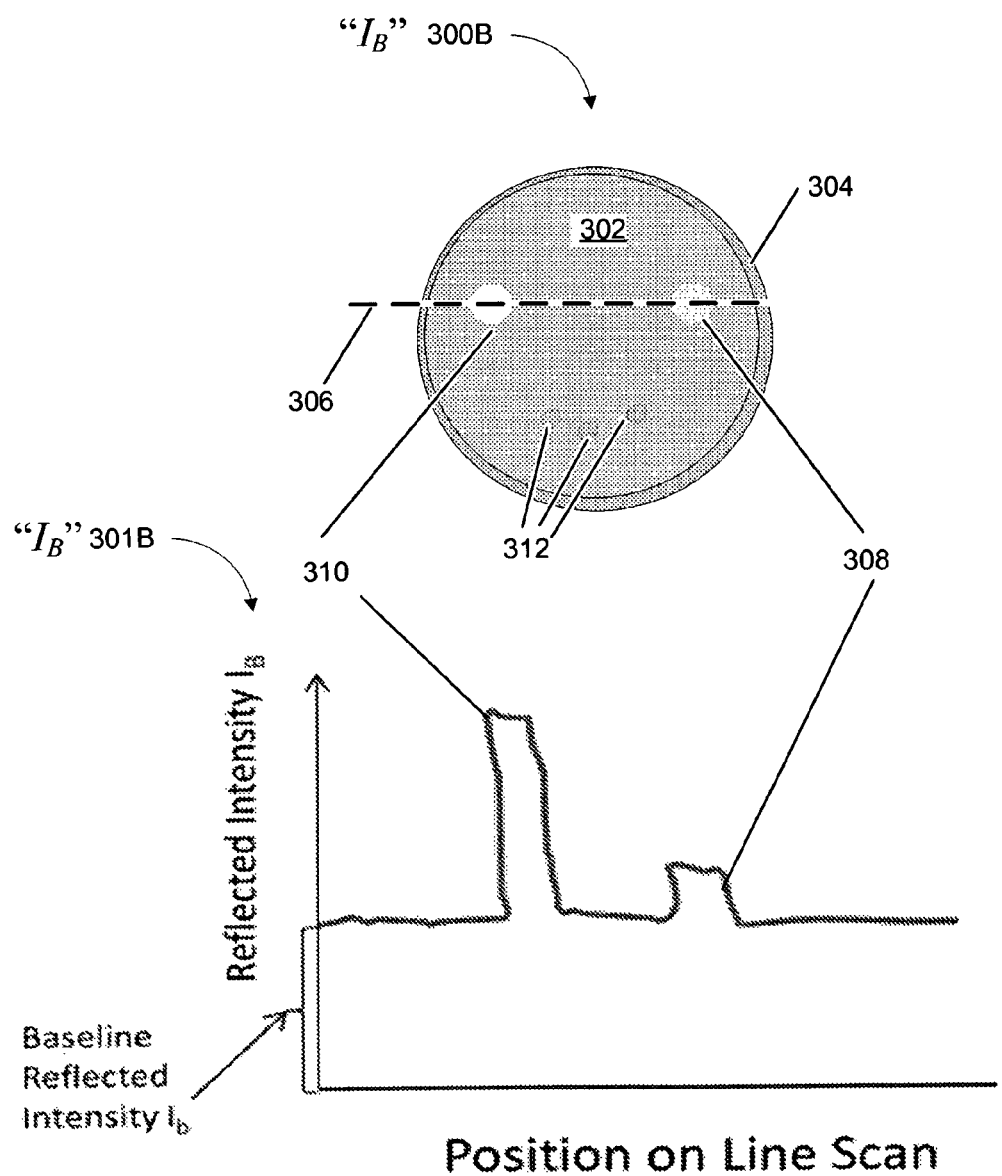
FIG. 3B shows a representative second reflected intensity image and a corresponding plot for a graphene sheet supported on a substrate.

FIG. 3B shows a representative second reflected intensity image and a corresponding plot for a graphene sheet supported on a substrate, arranged in accordance with at least some embodiments described herein. The representative second reflected intensity image 300B in FIG. 3B is of the graphene 302 supported on the substrate 304, with a corresponding plot 301B. A second reflected intensity image such as 300B may be obtained under bright field electromagnetic radiation at a second incident intensity. The second incident intensity may be greater than the first incident intensity by an amount sufficient to at least partly saturate an absorbance value of the saturable absorber. In various examples, the first and second incident intensities may be related by a ratio of the second incident intensity divided by the first incident intensity, which may have a value greater than 1:1, for example, 1.5:1, 2:1, 3:1, 4:1, 5:1, 10:1, 15:1, 20:1, 25:1, 30:1, 40:1, 50:1, 75:1, 100:1, 125:1, 150:1, 175:1, or 200:1. For example, in the case of graphene 302 and the first incident intensity employed in reflected intensity image 300A, a suitable second incident intensity may be about 50 Watts per square centimeter, for a ratio of the second incident intensity divided by the first incident intensity of 50/2.5=20:1.

In various examples, a second reflected intensity image such as 300B may appear lighter than a first reflected intensity image such as 300A because of the higher second incident intensity. However, gaps in graphene, such as area 308, may appear darker than substrate defects, such as area 310, corresponding to the lighter spot on substrate 304 that shows through graphene 302. The difference between graphene gaps and substrate defects represented by areas 308 and 310, respectively, may also be seen, for example in plot 301B according to peaks in the reflected intensity $I_B$ along axis 306 corresponding to areas 308 and 310. In plot 301B, the vertical axis may correspond to the second reflected intensity from the second intensity exposure, symbolized by $I_B$. The horizontal axis may correspond to the horizontal position on the reflected intensity image, such as in 300B along axis 306. The difference between graphene gaps and substrate defects represented by areas 308 and 310 may be explained by a greater reflectivity due to non-linear absorption for areas covered by a saturable absorbing such as graphene 302 at area 310 compared to gaps in graphene 302 at area 308. In reflected intensity image 300B, areas 312 may have their intensity vary proportional to the baseline if they are coated with graphene, or linearly if the debris is lying on top of the graphene.

Figure 3C:
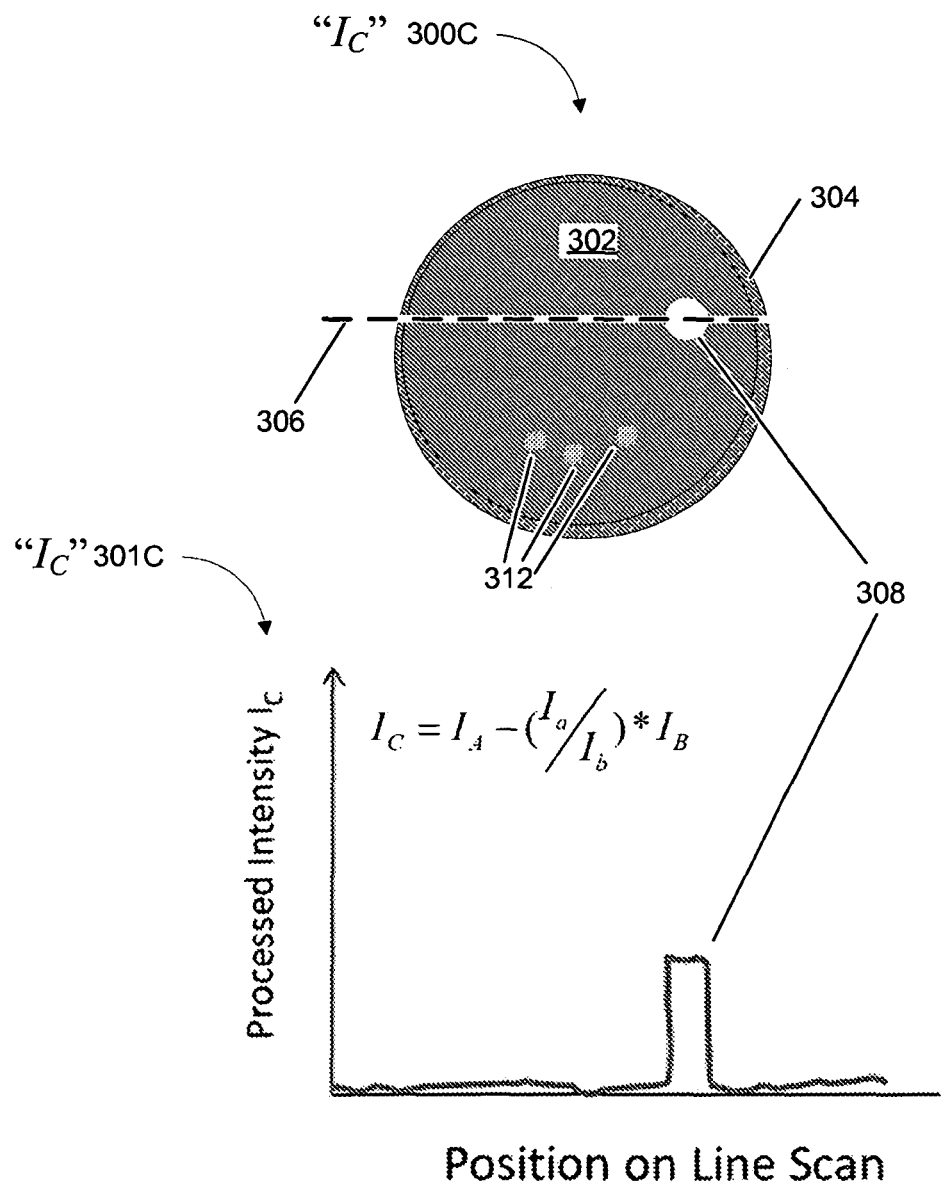
FIG. 3C shows a representative processed intensity image and a corresponding plot for a graphene sheet supported on a substrate as calculated from representative first and second reflected intensity images.

FIG. 3C shows a representative processed intensity image and corresponding plot of a graphene sheet supported on a substrate as calculated from first and second reflected intensity images, arranged in accordance with at least some embodiments described herein. The representative processed intensity image 300C in FIG. 3C is of the graphene 302 supported on the substrate 304, with a corresponding plot 301C. A processed intensity image such as 300C may be calculated from first and second reflected intensity images, such as 300A and 300B in FIG. 3A and FIG. 3B. Processed intensity images such as 300C may be calculated according to Equation (2.1):

$$I_C = I_A - (I_a/I_b) \cdot I_B \qquad (2.1)$$

In Equation (2.1), the symbol $I_A$ may represent the first reflected intensity obtained at the first incident intensity at any given location on the saturable absorber. The values of $I_A$ may be collectively displayed as an image (e.g., corresponding to first reflected intensity image 300A). The symbol $I_a$ may represent a first baseline reflected intensity of non-defect regions (e.g., regions of reflected intensity image 300A other than areas 308, 310, and 312). The symbol $I_B$ may represent the second reflected intensity obtained at the second incident intensity at any given location on the saturable absorber. The values of $I_B$ may also be collectively displayed as an image (e.g., corresponding to second reflected intensity image 300B). The symbol $I_b$ may represent a second baseline reflected intensity of non-defect regions coated with graphene (e.g., regions of reflected intensity image 300B other than areas 308, 310, and 312). The symbol $I_C$ may represent the processed intensity at any given location on the saturable absorber according to Equation 2.1. The values of $I_C$ may be collectively displayed as a processed intensity image, e.g. corresponding to processed intensity image 300C. The baseline reflected intensity values represented by symbols $I_b$ and $I_b$ may each be determined as an aggregate value of reflected intensity at non-defect regions coated with graphene (e.g., regions of reflected intensity image 300A or 300B, respectively, other than areas 308, 310, and 312). Such aggregate values may be determined as an average, a median, a mean, or some other representative aggregate value.

The processed intensity values according to equation 2.1 may be useful for the purpose of determining defects in graphene. By using Equation 2.1, substrate defects may be mathematically removed from the reflected intensity values to give the processed intensity $I_C$ and a corresponding processed intensity image. Consequently, a processed intensity image developed using $I_C$ according to Equation 2.1, such as image 300C, may show graphene gaps but not substrate defects. Thus, substrate defects (such as 310), which may be difficult to distinguish from graphene gaps (such as 308) in reflected intensity plots (such as 301A and 301B) and reflected intensity images (such as 300A and 300B) may be mathematically removed to provide processed intensity plots such as 301C and processed intensity images such as 300C.

For the purpose of determining defects in substrates using a graphene layer as an imaging aid, processed intensity may be calculated according to Equation 2.2:

$$I_{C.2} = I_B - (I_b/I_a) \cdot I_A \qquad (2.2)$$

In Equation (2.2), the symbols $I_A$, $I_B$, $I_a$, and $I_b$ have the same, values as in Equation (2.1). The processed intensity values represented by symbol $I_{C.2}$ differ from $I_C$ in having the effect of mathematically removing gaps in the saturable absorber from the processed intensity values. Consequently, an image developed using $I_{C.2}$ according to Equation 2.2 may show substrate defects such as 310 but not graphene gaps such as 308. In various examples, debris on the surface of a saturable absorber may appear similar to a gap in the saturable absorber, since the saturable absorber may be blocked by the debris from the optical path. Moreover, since debris may include saturable and non-saturable absorbing material, the procedure for generating a processed intensity image such as 300C may not remove such debris from the image, as shown by areas of debris 312 in processed intensity image 300C.

Figure 3D:
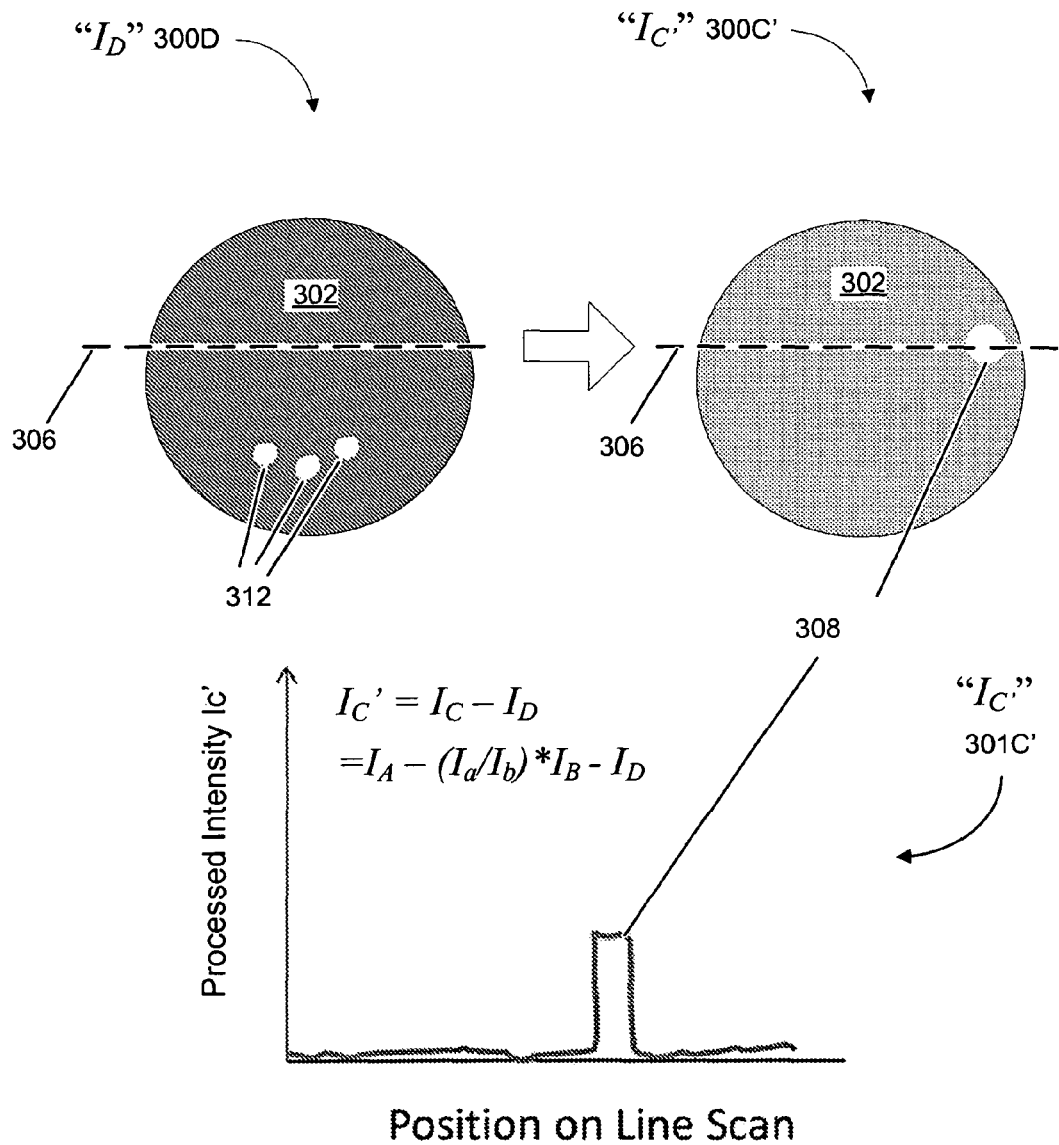
FIG. 3D shows a representative dark field image highlighting surface debris and removal of the debris in a processed image.

FIG. 3D shows a representative dark field image highlighting surface debris and mathematical removal of the debris in a processed image, in accordance with at least some embodiments herein. The representative dark field image 300D and representative processed intensity image 300C' in FIG. 3D are of the graphene 302 supported on the substrate 304, with a corresponding plot 301C'. A processed intensity image such as 300C' may be calculated may be calculated according to Equation (3.1):

$$I_C' = I_C - I_D = (I_A - (I_a/I_b) \cdot I_B) \cdot I_D \qquad (3.1)$$

In Equation (3.1), the symbol $I_D$ may represent the reflected intensity obtained under dark field illumination at any given location on the saturable absorber, which may be collectively represented in a dark field image such as 300D. The values of $I_D$ may be collectively displayed as an image (e.g., corresponding to reflected intensity image 300D). The symbol $I_C'$ may represent the processed intensity at any given location on the saturable absorber according to Equation 3.1. The values of $I_C'$ may be collectively displayed as a processed intensity image, e.g. corresponding to processed intensity image 300C'.

The processed intensity values according to equation 3.1 may be useful for the purpose of determining defects in graphene. By using Equation 3.1, surface debris may be mathematically removed from the processed intensity $I_C$ to give the processed intensity $I_C'$ and a corresponding corrected processed intensity image. Consequently, an image developed using $I_C$ according to Equation 3.1, such as image 300C', may show graphene gaps but not surface debris. Thus, surface debris (such as 312) and substrate defects (such as 310), which may be difficult to distinguish from graphene gaps (such as 308) in reflected intensity plots (such as 301A, 301B, and 301C) and reflected intensity images (such as 300A, 300B, and 300C) may be mathematically removed to provide processed intensity plots such as 301C and processed intensity images such as 300C.

For the purpose of determining defects in substrates using a graphene layer as an imaging aid, processed intensity may be calculated according to Equation 3.2:

$$I_{C.2}' = I_{C.2} - I_D = (I_B - (I_b/I_a) \cdot I_a) - I_D \qquad (3.2)$$

In Equation (3.2), the symbols $I_A$, $I_B$, $I_D$, $I_a$, and $I_b$ have the same values as in Equation (3:1). The processed intensity values represented by symbol $I_{C.2}$ and $I_{C.2}'$ differ from $I_C$ and $I_C'$ in having the effect of mathematically removing gaps in the saturable absorber from the processed intensity values. Consequently, an image developed using $I_{C.2}'$ according to Equation 3.2 may show substrate defects such as 310 but not graphene gaps such as 308 or surface debris such as 312.

Figure 3E:
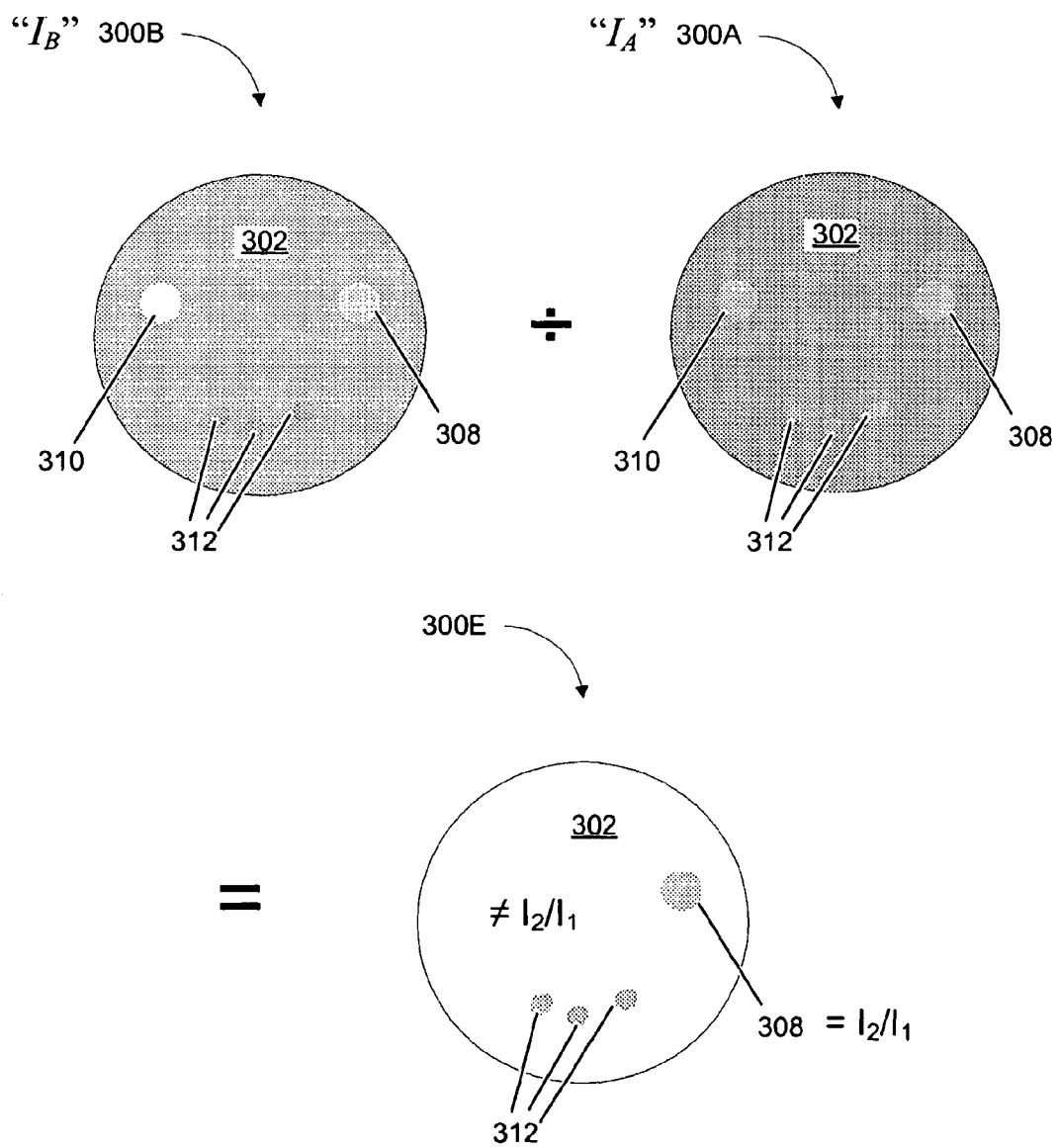
FIG. 3E illustrates alternate example operations for detecting one or more defects in a saturable absorber.

FIG. 3E illustrates alternate example operations for detecting one or more defects in a saturable absorber, arranged in accordance with at least some embodiments described herein. In several examples, one or more defects in a saturable absorber such as graphene 302 may be detected as illustrated in FIG. 3E. As described for FIG. 3A and FIG. 3B, first and second reflected intensity images 300A and 300B of a saturable absorber such as graphene 302 may be acquired under bright field electromagnetic radiation at first and second incident intensities. As described for FIG. 3A and FIG. 3B, the second incident intensity may be greater than the first incident intensity by an amount sufficient to at least partly saturate an absorbance value of the saturable absorber, e.g., graphene 302. An incident intensity ratio $I_R$ may correspond to the second incident intensity $I_2$ divided by the first incident intensity $I_1$ according to Equation (4)

$$I_R = I_2/I_1 \qquad (4)$$

In various examples, a reflected intensity ratio map 300E may be calculated corresponding to the second reflected intensity image 300B divided by the first reflected intensity image 300A. Regions of the reflected intensity ratio map 300E that may be equal or substantially equal to the incident intensity ratio $I_R$ may be identified as defects, for example, area 308. Regions of the reflected intensity ratio map 300E that may be greater than the incident intensity ratio $I_R$ may be identified as areas absent defects, e.g., the white areas of reflected intensity ratio map 300E excluding areas 308 and 312. In some examples, where debris may be present, such as in areas 312, the debris may be excluded from the image map by correcting with a dark field image such as 300D, as described for FIG. 3D. In some examples, the image map may be converted to an explicit processed intensity image such as 300C or 300C'.

In addition or alternatively to the calculations and processing described for Equations 2.1, 2.2., 3.1 3.2, and/or 4, look-up tables or other predetermined data for defects may be employed. For example, historical data may be used to collect or calculate standard correction factors for use in a look-up table or database. In some examples, defect characteristics such as size, shape, and/or saturable/nonsaturable character may be collected for typical or expected defects, and may be incorporated in the look-up table or database.

In various examples, images such as 300A, 300B, and 300D may be obtained from any suitable imaging apparatus, for example, a confocal imaging apparatus, a line scanning apparatus, or a raster scan.

Figure 4A:
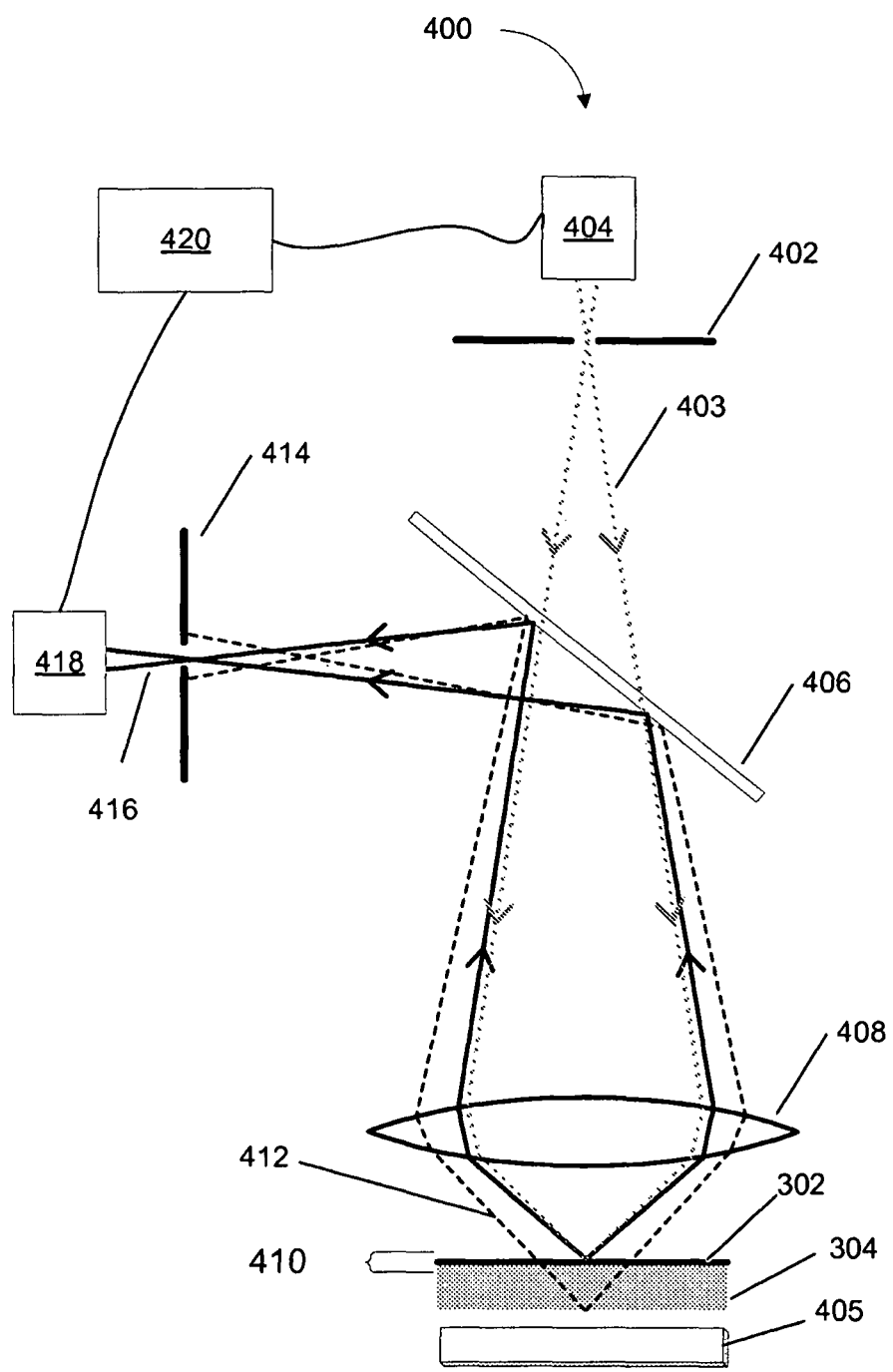
FIG. 4A is a conceptual drawing representing various confocal imaging apparatus that may be employed to image a saturable absorber.

FIG. 4A is a conceptual drawing representing various confocal imaging apparatus that may be employed to image a saturable absorber, arranged in accordance with at least some embodiments described herein FIG. 4A shows a confocal imager 400 that may be employed to image a saturable absorber such as graphene 302 on a substrate 304. In various examples, confocal imager 400 may include: an illumination aperture 402; an illumination source 404 configured to emit illumination 403; a sample holder 405 configured to hold, e.g., graphene 302; a beam splitter 406; at least one lens 408 configured to focus illumination 403 to a sample at sample holder 405; a focal plane 410 at the sample holder 405; an imaging aperture 414 configured to block out-of-focal-plane reflected light 412 and selectively pass in-focal-plane reflected light 416; a detector 418; and a controller 420 operatively coupled to the illumination source 404 and the detector 418.

In some examples, illumination source 404 may be any suitable device for providing electromagnetic radiation in a range where graphene 302 displays saturable absorbance. Examples of illumination source 404 may include a laser, a light emitting diode, a xenon lamp, or the like. Illumination source 404 may be broadband, narrowband, or monochromatic. Illumination source 404 may optionally include a filter or grating to select desired wavelengths or wavelength ranges.

In several examples, sample holder 405 may be configured to hold a saturable absorber such as graphene 302 along with substrate 304. In some examples, sample holder 405 may be substrate 304.

In various examples, illumination aperture 402 may admit illumination 403 from illumination source 404 to a beam splitter 406 and at least one lens 408 to graphene 302 at a substrate 304. Light may be reflected from graphene 302 at a substrate 304 back through lens 408 and may be reflected off of beam splitter 406. In-focal-plane reflected light 416 within a focal plane 410 may be reflected off of beam splitter 406 and may be admitted by imaging aperture 414 to detector 418. Out-of-focal plane reflected light 412, which is out of the focal plane 410, may be reflected off of beam splitter 406 and may be blocked by imaging aperture 414. The controller 420 may be configured to operate illumination source 404 and to acquire images and reflection intensities at detector 418. One or more of the various optical elements of confocal imager 400, including illumination aperture 402, illumination source 404, beam splitter 406, lens 408, sample holder 405, imaging aperture 414, and/or detector 418 may be angled relative to each other to provide on-axis bright field illumination, and to provide off-axis dark field illumination to a sample at sample holder 405.

Figure 4B:
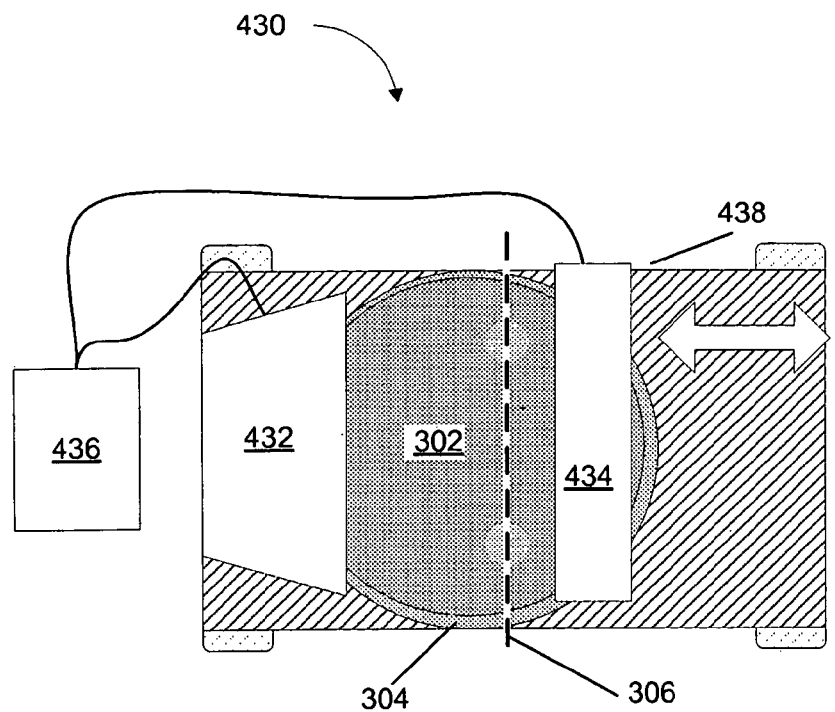
FIG. 4B is a top view of a conceptual drawing representing various scanning apparatus that may be employed to image a saturable absorber.
Figure 4C:
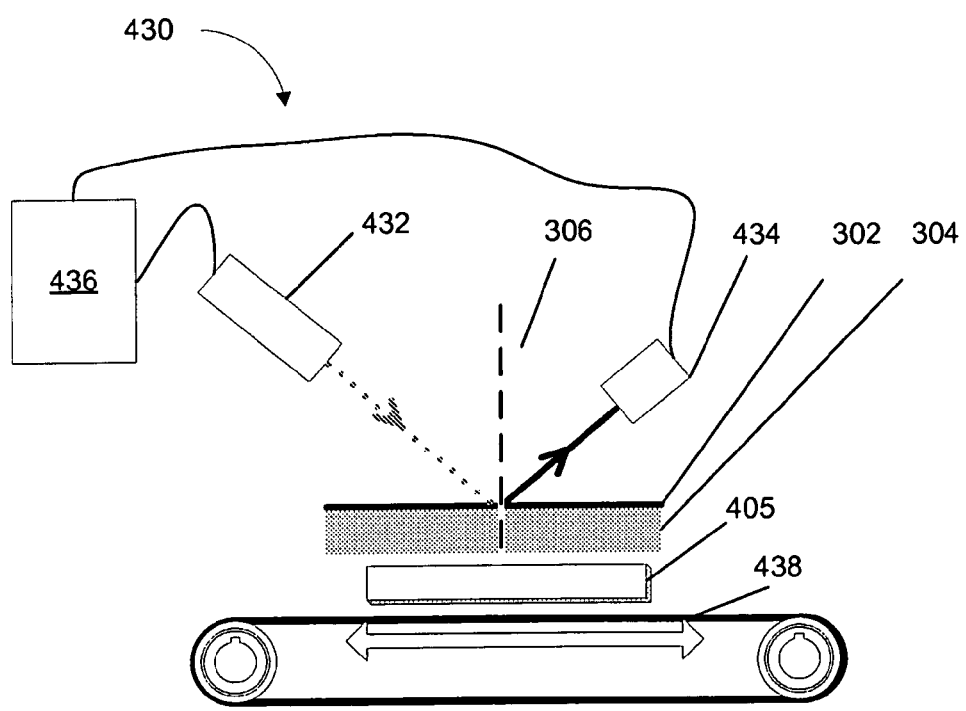
FIG. 4C is a side view of the scanning apparatus illustrated in FIG. 4B.

FIG. 4B is a top view of a conceptual drawing representing various scanning apparatus 430 that may be employed to image a saturable absorber, arranged in accordance with at least some embodiments described herein. FIG. 4C is a side view of the scanner apparatus 430 illustrated in FIG. 4B, arranged in accordance with at least some embodiments described herein. In various examples, scanner apparatus 430 may include: an illumination source 432 configured to illuminate a sample at sample holder 405 at an incident angle; a detector 434 configured to detect light reflected from a sample; a translation/rotation mechanism 438; and a controller 436 operatively coupled to the illumination source 432; the detector 434; and the translation/rotation mechanism 438.

In some examples, scanner 430 may include the illumination source 432 configured to illuminate a sample at sample holder 405 at an incident angle. The illumination source 432 may be configured to selectively direct illumination along axis 306, for example, using a beam spreader, a lens, a light pipe, or a scanning mirror configured to raster/illuminate along axis 306.

In several examples, scanner 430 may also include the detector 434 configured to detect light reflected from a sample such as graphene 302 at sample holder 405.

The sample holder 405 may be configured together with the translation/rotation mechanism 438 as a mobile sample stage suitable for translating and/or rotating a sample relative to illumination source 432 and detector 434. In some examples, the sample holder 405 may be stationary and the illumination source 432 and the detector 434 may be moved relative to the sample holder 405 by the translation/rotation mechanism 438. The sample holder 405, the illumination source 432 and the detector 434 may be angled relative to each other to provide on-axis, bright field illumination and off-axis, dark field illumination to a sample at sample holder 405. The controller 436 may be included to operate the illumination source 432; acquire images and reflection intensities at the detector 434; adjust angles to provide the on-axis, bright field illumination and off-axis, dark field illumination; and operate the translation/rotation mechanism 438.

Figure 5:
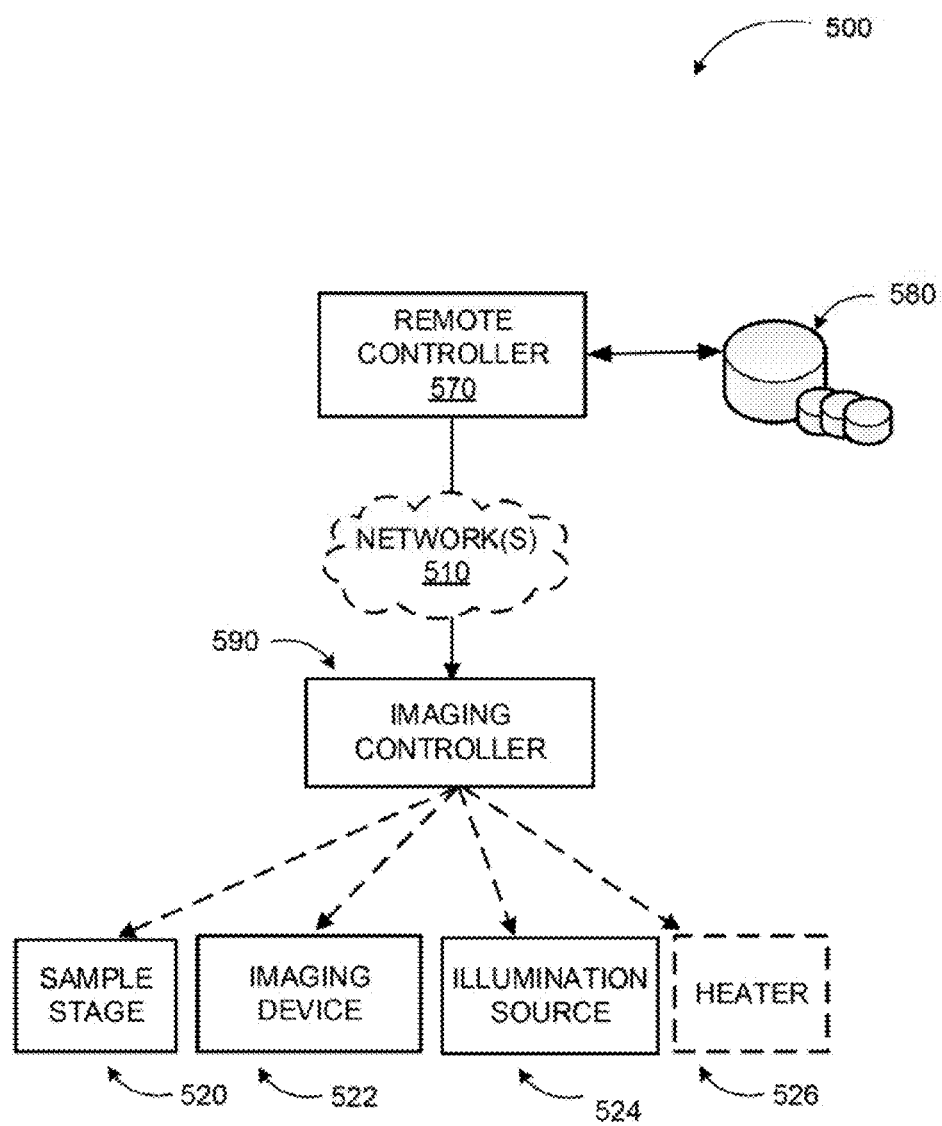
FIG. 5 is a block diagram of representing various automated machines that may be used for carrying out the described method of detecting defects in a saturable absorber.
Figure 6:
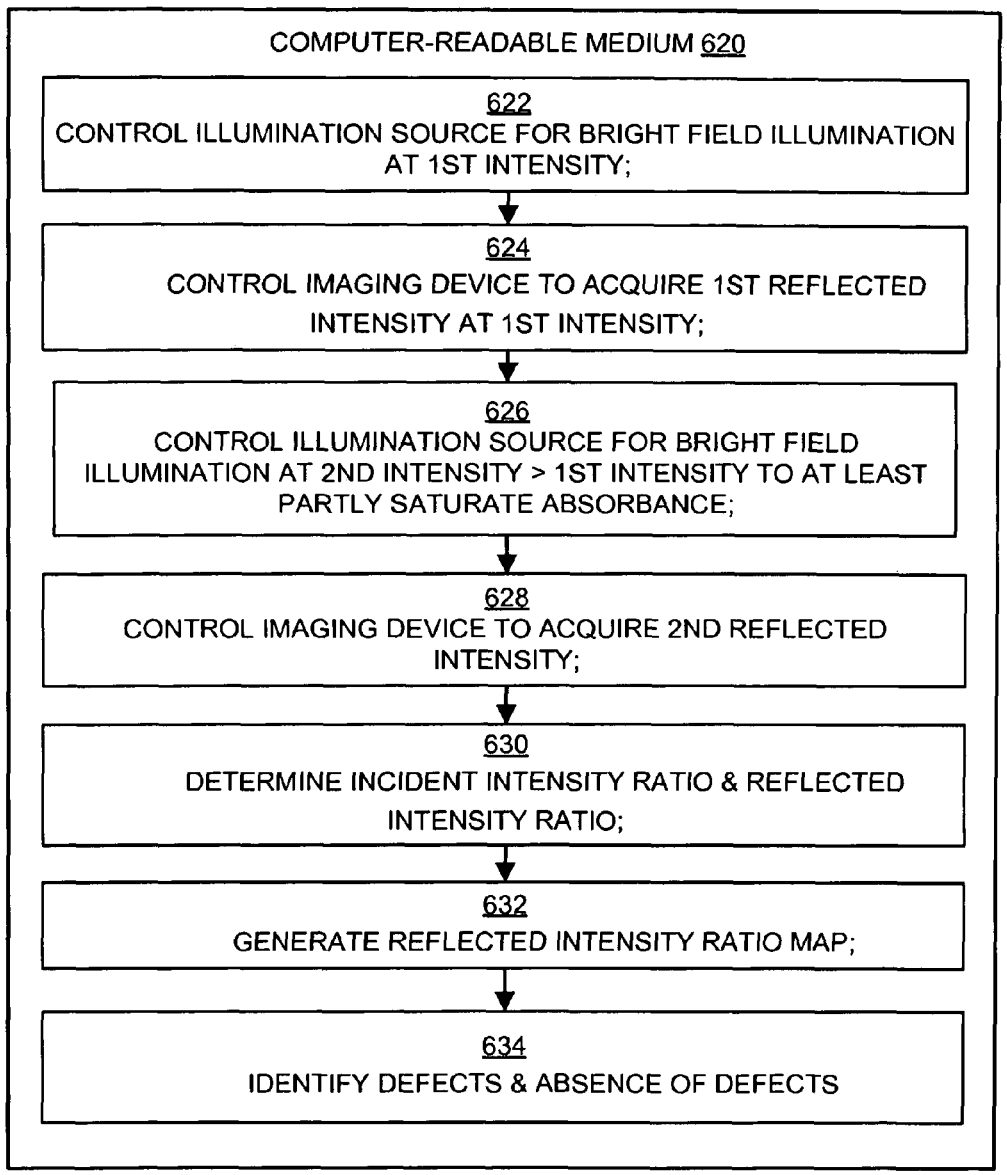
FIG. 6 is an example flow diagram showing example blocks that may be used for carrying out the described method of detecting defects in a saturable absorber.

FIG. 5 is a block diagram representing various automated machines 500 that may be used for carrying out the described method of detecting defects in a saturable absorber using the process steps outlined in FIG. 6, arranged in accordance with at least some embodiments described herein. As illustrated in FIG. 5, an imaging controller 590 may be coupled to the machines that may be used to carry out the process outline described in FIG. 6, for example, sample stage 520, an imaging detector 522, an illumination device 524, and an optional heater 526. Imaging controller 590 may be operated by human control, by a remote controller 570 via network 510, or by machine executed instructions such as might be found in a computer program. Data associated with controlling the different processes of imaging one or more defects in a saturable absorber may be stored at and/or received from data stores 580.

In various examples, imaging controller 590, sample stage 520, imaging device 522, and illumination device 524 may together represent any imaging system suitable for carrying out the methods described herein. For example, suitable imaging systems may include confocal imager 400 of FIG. 4A or scanner 430 of FIG. 4B and FIG. 4C. For example, with respect to confocal imager 400, imaging controller 590 may correspond to controller 420; sample stage 520 may correspond to sample holder 405; illumination device 524 may correspond to illumination source 404 and illumination aperture 402; imaging device 522 may correspond collectively to beam splitter 406, lens 408, imaging aperture 414, and detector 418. In another example, with respect to scanner 430, imaging controller 590 may correspond to controller 436; sample stage 520 may correspond to sample holder 405 and translation/rotation mechanism 438; illumination device 524 may correspond to illumination source 432; and imaging device 522 may correspond to detector 434.

In several examples, the individual elements of imaging system 500 may be implemented as any suitable device configured in any suitable fashion for carrying out the operations described herein. For example, sample stage 520 may be stationary or may include one or more moving functions, such as translation in zero, one, two, or three perpendicular axes, rotation in one, two, or three perpendicular axes, combinations thereof, and the like. Such moving functions may be provided by motors, linear actuators, piezoelectric actuators, or the like. Likewise, illumination source 524 may be any source of electromagnetic radiation that may elicit saturable absorbance in the saturable absorber sample. Suitable sources of electromagnetic radiation include, for example, lasers, light emitting diodes, lamps such as a xenon lamp or mercury lamp, or the like. Similarly, imaging device 522 may be a charge coupled device in linear or two dimensional form or a complementary metal oxide semiconductor imaging device in linear or two dimensional form; a photomultiplier tube; or any other device suitable for detecting the electromagnetic radiation produced by the illumination source and reflected, scattered or diffused from the sample. The illumination source 524 and imaging device 522 may separately or together include any optical element suited for carrying out the methods described herein, such as lenses, mirrors, waveguides, beam splitters, optical gratings, or the like.

Various example embodiments may also include methods of imaging one or more defects in a saturable absorber as described herein. These methods may be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. The various human operators need not be collocated with each other, and instead each operated can be located about one or more machines that perform a portion of the operations. In other examples, the human interaction may be automated such as by pre-selected criteria that may be machine automated.

FIG. 6 is an example flow diagram showing example blocks that may be used for carrying out the described method of detecting defects in a saturable absorber, arranged in accordance with at least some embodiments described herein. In various examples, a process of imaging one or more defects in a saturable absorber as described herein may include one or more operations, functions or actions as is illustrated by one or more of blocks 622, 624, 626, 628, 630, 632, and/or 634. Various example methods of imaging one or more defects in a saturable absorber as described herein may be controlled by a computing device such as computing device 700 in FIG. 7 or a special purpose controller such as imaging controller 590 of FIG. 5. Controller device 610 may be embodied as computing device 700, imaging controller 590, or similar devices configured to execute instructions stored in computer-readable medium 620 for controlling the performance of the method Some example processes may begin with block 622, "CONTROL ILLUMINATION SOURCE FOR BRIGHT FIELD ILLUMINATION AT 1ST INTENSITY", where the sample may be illuminated with electromagnetic radiation at a first incident intensity from an illumination source such as the illumination source 432 of FIG. 4B.

Block 622 may be followed by block 624, "CONTROL IMAGING DEVICE TO ACQUIRE 1ST REFLECTED INTENSITY AT 1ST INTENSITY", where light reflected from the sample at the first reflected intensity may be detected at a detector such as the detector 434 of FIG. 4B.

Block 624 may be followed by block 626, "CONTROL ILLUMINATION SOURCE FOR BRIGHT FIELD ILLUMINATION AT 2ND INTENSITY>1ST INTENSITY TO AT LEAST PARTLY SATURATE ABSORBANCE". The second incident intensity may be configured to be greater than the first incident intensity by an amount sufficient to at least partly saturate an absorbance value of a saturable absorber at the sample holder, for example, graphene 302.

Block 626 may be followed by block 628, "CONTROL IMAGING DEVICE TO ACQUIRE 2ND REFLECTED INTENSITY", where light reflected from the sample at the first reflected intensity may be detected at a detector such as the detector 434 of FIG. 4B.

Block 628 may be followed by block 630, "DETERMINE INCIDENT INTENSITY RATIO & REFLECTED INTENSITY RATIO". The incident intensity ratio may be determined by dividing the second incident intensity by the first incident intensity. The reflected intensity ratio may be determined by dividing the second reflected intensity image by the first reflected intensity image. The reflected intensity ratio may be presented or calculated as an average intensity of the second reflected intensity image divided by an average of the first reflected intensity image. The calculated incident intensity ratio and the reflected intensity ratio may be retained for use in additional operations.

Block 630 may be followed by block 632, "GENERATE REFLECTED INTENSITY RATIO MAP". The reflected intensity ratio map may be determined for the saturable absorber by determining reflected intensity ratios for a plurality of locations on the saturable absorber. The reflected intensity ratio map may be generated as numerical data, and may also be stored or presented in graphical form, for example, as an image corresponding to the intensity ratio map.

Block 632 may be followed by block 634, "IDENTIFY DEFECTS & IDENTIFY ABSENCE OF DEFECTS". Defects may be identified at one or more locations on the saturable absorber where the reflected intensity ratio may be equal or substantially equal to the incident intensity ratio. Absence of defects may be identified at one or more locations on the saturable absorber where the reflected intensity ratio may be greater than the incident intensity ratio.

Data regarding the defects, for example, location, size, nature of the defect, or the like, may be stored and outputted for use by human or automated processing. For example, locations of defects in a saturable absorber may be provided as quality control feedback to a manufacturing process. In another example, manufactured articles of saturable absorbers may be sorted according to the number and types of defects detected.

The operations included in the process of FIG. 6 described above are for illustration purposes. A process of imaging one or more defects in a saturable absorber as described herein may be implemented by similar processes with fewer or additional operations. In some examples, the operations may be performed in a different order. In some other examples, various operations may be eliminated. In still other examples, various operations may be divided into additional operations, or combined together into fewer operations. Although illustrated as sequentially ordered operations, in some implementations the various operations may be performed in a different order, or in some cases various operations may be performed at the same or substantially the same time. For example, any other similar process may be implemented with fewer, different, or additional operations so long as such similar processes may identify defects in a saturable absorber by distinguishing locations in a sample according to extent of saturable absorbance properties. For example, one alternate process may follow operations 622, 624, and 626 with the following operations: computing a processed intensity image from the first and second reflected intensity images according to the following formula: $I_C = I_A - (I_a/I_b) \cdot I_B$. The symbol $I_C$ may represent the processed intensity image. The symbol $I_A$ may represent the first reflected intensity image. The symbol $I_B$ may represent the second reflected intensity image. The symbol $I_a$ may represent a first baseline reflected intensity of the saturable absorber under bright field electromagnetic radiation at the first incident intensity. The symbol $I_b$ may represent a second baseline reflected intensity of the saturable absorber under bright field electromagnetic radiation at the second incident intensity. The first and second baseline intensities may represent any suitable aggregate value for defect-free regions of the saturable absorber, for example, average, median, or mean intensity values. In addition or alternatively to the above calculation, look-up tables or other predetermined data for defects may be employed. In this process, the processed intensity image may depict defects in the saturable absorber.

Figure 7:
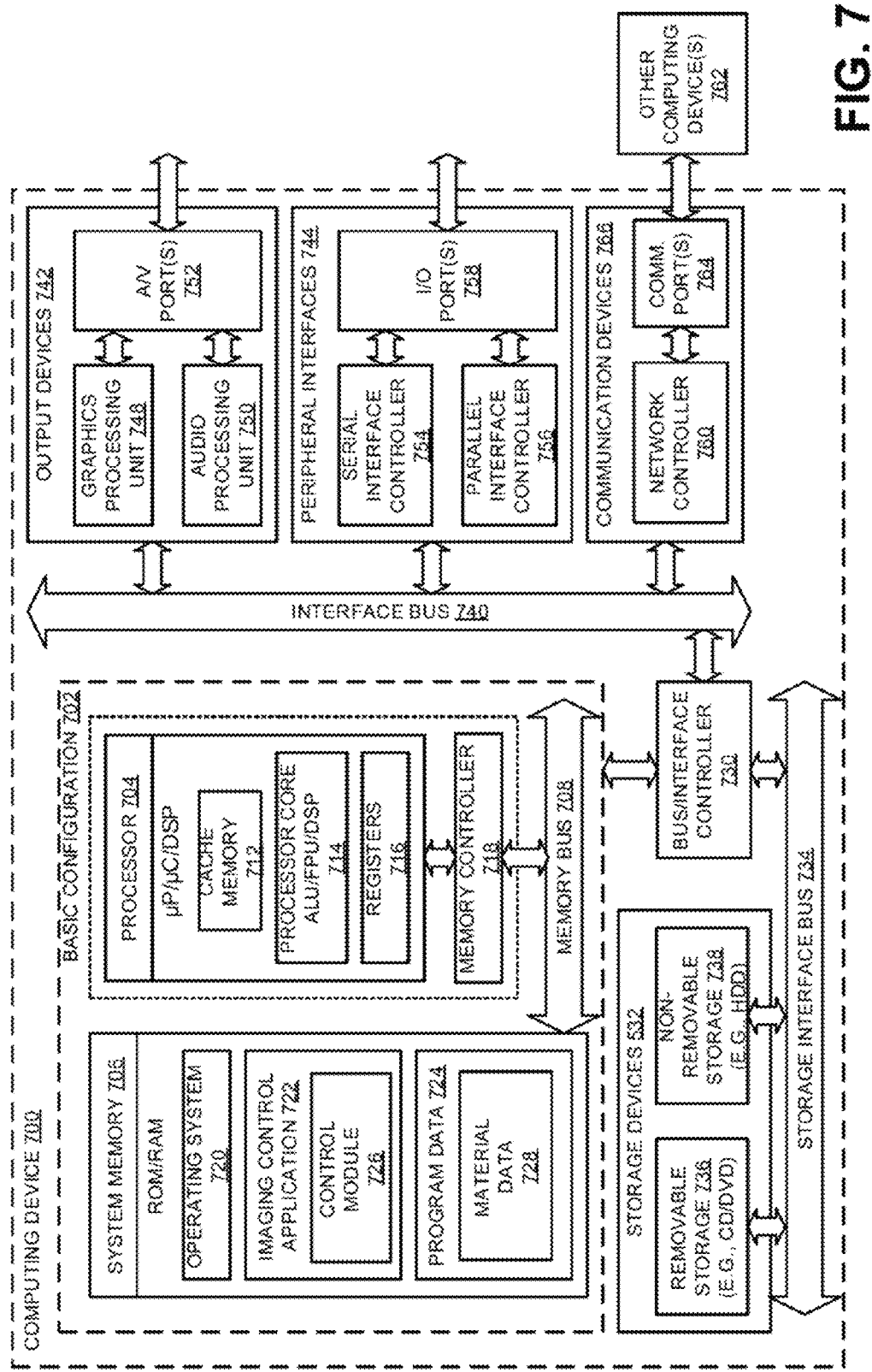
FIG. 7 illustrates an example general purpose computing device that may be used to control the automated machine of FIG. 5 or similar equipment in carrying out the described method of detecting defects in a saturable absorber.

FIG. 7 illustrates an example general purpose computing device that may be used to control the automated machine 500 of FIG. 5 or similar imaging equipment in carrying out the described method of detecting defects in a saturable absorber, arranged in accordance with at least some embodiments described herein. In a basic configuration 702, computing device 700 typically may include one or more processors 704 and a system memory 706. A memory bus 708 may be used for communicating between processor 704 and system memory 706.

Depending on the desired configuration, processor 704 may be of any type including but not limited to a microprocessor (μP), a microcontroller (μC), a digital signal processor (DSP), or any combination thereof. Processor 704 may include one more levels of caching, such as a level cache memory 712, a processor core 714, and registers 716. Processor core 714 may include an arithmetic logic unit (ALU), a floating point unit (FPU), a digital signal processing core (DSP Core), or any combination thereof. An example memory controller 718 may also be used with processor 704, or in some implementations memory controller 715 may be an internal part of processor 704.

Depending on the desired configuration, system memory 706 may be of any type including but not limited to volatile memory (such as RAM), non-volatile memory (such as ROM, flash memory, etc.) or any combination thereof. System memory 706 may include an operating system 720, one or more imaging control applications 722, and program data 724. Imaging control application 722 may include a control module 726 that may be arranged to control imaging system 500 of FIG. 5 and any other processes, methods and functions as discussed above. Program data 724 may include, among other data, material data 728 for controlling various aspects of the imaging system 500. This described basic configuration 702 is illustrated in FIG. 7 by those components within the inner dashed line.

Computing device 700 may have additional features or functionality, and additional interfaces to facilitate communications between basic configuration 702 and any required devices and interfaces. For example, a bus/interface controller 730 may be used to facilitate communications between basic configuration 702 and one or more data storage devices 732 via a storage interface bus 734. Data storage devices 732 may be removable storage devices 736, non-removable storage devices 738, or a combination thereof. Examples of removable storage and non-removable storage devices may include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 706, removable storage devices 736 and non-removable storage devices 738 may be examples of computer storage media. Computer storage media may include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of computing device 700.

Computing device 700 may also include an interface bus 740 for facilitating communication from various interface devices (e.g., output devices 742, peripheral interfaces 744, and communication devices 766 to basic configuration 702 via bus/interface controller 730. Output devices 742 may include a graphics processing unit 748 and an audio processing unit 750, which may be configured to communicate to various external devices such as a display or speakers via one or more A/V ports 752. Example peripheral interfaces 744 include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. A communication device 766 may include a network controller 760, which may be arranged to facilitate communications with one or more other computing devices 762 over a network communication link via one or more communication ports 764.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 700 may be implemented as a portion of a physical server, virtual server, a computing cloud, or a hybrid device that include any of the above functions. Computing device 700 may also be implemented as a personal computer including both laptop computer and non-laptop computer configurations. Moreover computing device 700 may be implemented as a networked system or as part of a general purpose or specialized server.

Networks for a networked system including computing device 700 may comprise any topology of servers, clients, switches, routers, modems, Internet service providers, and any appropriate communication media (e.g., wired or wireless communications). A system according to embodiments may have a static or dynamic network topology. The networks may include a secure network such as an enterprise network (e.g., a LAN, WAN, or WLAN), an unsecure network such as a wireless open network (e.g., IEEE 802.11 wireless networks), or a world-wide network such (e.g., the Internet). The networks may also comprise a plurality of distinct networks that may be adapted to operate together. Such networks may be configured to provide communication between the nodes described herein. By way of example, and not limitation, these networks may include wireless media such as acoustic, RF, infrared and other wireless media. Furthermore, the networks may be portions of the same network or separate networks.

Figure 8:
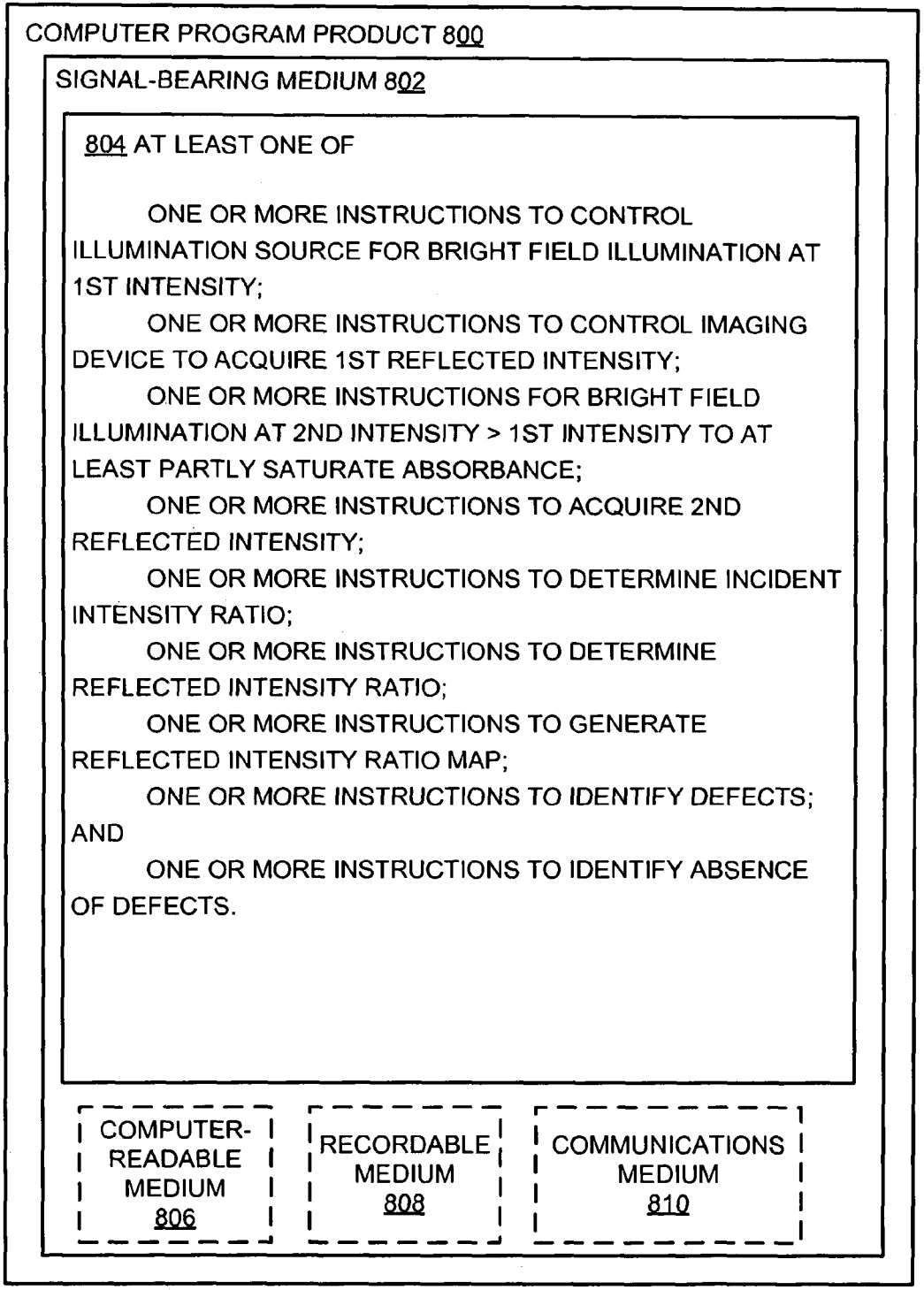
FIG. 8 illustrates a representative block diagram of an example computer program product that may be used to control the automated machine of FIG. 5 or 7 or similar equipment in carrying out the described method of detecting defects in a saturable absorber.

FIG. 8 illustrates a representative block diagram of an example computer program product that may be used to control the automated machine of FIG. 7 or similar equipment in carrying out the described method of detecting defects in a saturable absorber, arranged in accordance with at least some embodiments described herein. In some examples, as shown in FIG. 8, computer program product 800 may include a signal bearing medium 802 that may also include machine readable instructions 804 that, when executed by, for example, a processor, may provide the functionality described above with respect to FIG. 5 through FIG. 7. For example, referring to imaging controller 590, one or more of the tasks shown in FIG. 8 may be undertaken in response to machine readable instructions 804 conveyed to the imaging controller 590 by signal bearing medium 802 to perform actions associated with imaging one or more defects in a saturable absorber as described herein. Some of those instructions may include, for example, one or more instructions to: "control illumination source for bright field illumination at 1st intensity"; "control imaging device to acquire 1st reflected intensity image"; for "bright field illumination at 2nd intensity>1st intensity to at least partly saturate absorbance"; "acquire 2nd reflected intensity image"; "determine incident intensity ratio"; "determine reflected intensity ratio"; "generate reflected intensity ratio map"; "identify defects where reflected intensity ratio may be equal or substantially equal to the incident intensity ratio; and "identify absence of defects where the reflected intensity ratio> the incident intensity ratio".

In some implementations, signal bearing medium 802 depicted in FIG. 8 may encompass a computer-readable medium 806, such as, but not limited to, a hard disk drive, a Compact Disc (CD), a Digital Versatile Disk (DVD), a digital tape, memory, etc. In some implementations, signal bearing medium 802 may encompass a recordable medium 808, such as, but not limited to, memory, read/write (R/W) CDs, R/W DVDs, etc. In some implementations, signal bearing medium 802 may encompass a communications medium 810, such as, but not limited to, a digital and/or an analog communication medium (e.g., a fiber optic cable, a waveguide, a wired communications link, a wireless communication link, etc.). For example, computer program product 800 may be conveyed to the processor 704 by an RF signal bearing medium 802, where the signal bearing medium 802 may be conveyed by a communications medium 810 (e.g., a wireless communications medium conforming with the IEEE 802.11 standard). While the embodiments will be described in the general context of program modules that execute in conjunction with an application program that runs on an operating system on a personal computer, those skilled in the art will recognize that aspects may also be implemented in combination with other program modules.

Generally, program modules include routines, programs, components, data structures, and other types of structures that perform particular tasks or implement particular abstract data types. Moreover, those skilled in the art will appreciate that embodiments may be practiced with other computer system configurations, including hand-held devices, multiprocessor systems, microprocessor-based or programmable consumer electronics, minicomputers, mainframe computers, and comparable computing devices. Embodiments may also be practiced in distributed computing environments where tasks may be performed by remote processing devices that may be linked through a communications network. In a distributed computing environment, program modules may be located in both local and remote memory storage devices.

Embodiments may be implemented as a computer-implemented process (method), a computing system, or as an article of manufacture, such as a computer program product or computer readable media. The computer program product may be a computer storage medium readable by a computer system and encoding a computer program that comprises instructions for causing a computer or computing system to perform example process(es). The computer-readable storage medium can for example be implemented via one or more of a volatile computer memory, a non-volatile memory, a hard drive, a flash drive, a floppy disk, or a compact disk, and comparable media.

Throughout this specification, the term "platform" may be a combination of software and hardware components for providing a configuration environment, which may facilitate configuration of software/hardware products and services for a variety of purposes. Examples of platforms include, but are not limited to, a hosted service executed over a plurality of servers, an application executed on a single computing device, and comparable systems. The term "server" generally refers to a computing device executing one or more software programs typically in a networked environment. However, a server may also be implemented as a virtual server (software programs) executed on one or more computing devices viewed as a server on the network. More detail on these technologies and example operations is provided below.

Some examples embodiments may include various methods of imaging one or more defects in a saturable absorber. Example methods may include acquiring a first reflected intensity of a saturable absorber for a location on the saturable absorber under bright field electromagnetic radiation at a first incident intensity, and acquiring a second reflected intensity of the saturable absorber for the location under bright field electromagnetic radiation at a second incident intensity. The second incident intensity may be greater than the first incident intensity by an amount sufficient to at least partly saturate an absorbance value of the saturable absorber. The example methods may also include determining an incident intensity ratio corresponding to the second incident intensity divided by the first incident intensity; determining a reflected intensity ratio for the location corresponding to the second reflected intensity divided by the first reflected intensity; generating a reflected intensity ratio map for the saturable absorber by determining reflected intensity ratios for a plurality of locations on the saturable absorber; and comparing the reflected intensity ratio to the incident intensity ratio to identify one or more defects at one or more of the plurality of locations.

In various examples, the methods may include identifying an absence of defects at a location on the saturable absorber where the reflected intensity ratio may be greater than the incident intensity ratio. The reflected intensity ratio map may be an image of the one or more defects. The saturable absorber may include one or more of: graphene, a semiconductor, and a metal. The incident intensity ratio may be from about 2:1 to about 200:1 The first and second incident intensities of the electromagnetic radiation may have a peak value from about 0.1 Megawatts per square centimeter to about 100 Megawatts per square centimeter. The first and second incident intensities of the electromagnetic radiation may have an average value from about 0.1 Watts per square centimeter to about 500 Watts per square centimeter. The electromagnetic radiation may have a wavelength from about 1 nanometer to about 1 millimeter. The electromagnetic radiation may be monochromatic. The electromagnetic radiation may be provided by one of: a laser, a light emitting diode, a xenon lamp, and/or a microwave source.

In some examples, the methods may include computing a processed intensity from the first and second reflected intensities according to the following formula:

$$I_C = I_A - (I_a/I_b)I_B$$

where: $I_C$ may represent the processed intensity; $I_A$ may represent the first reflected intensity; $I_B$ may represent the second reflected intensity; $I_a$ may represent a first baseline reflected intensity of the saturable absorber under bright field electromagnetic radiation at the first incident intensity; and $I_b$ may represent a second baseline reflected intensity of the saturable absorber under bright field electromagnetic radiation at the second incident intensity.

In several examples, the methods may include acquiring a third reflected intensity of the saturable absorber for the location under dark field electromagnetic radiation at a third incident intensity; and computing a corrected processed intensity according to the following formula:

$$I_C' = I_C - I_D = I_A - (I_a/I_b) \cdot I_B - I_D$$

where: $I_C'$ may represent the corrected processed intensity; and $I_D$ may represent the third reflected intensity of the saturable absorber for the location under dark field electromagnetic radiation at the third incident intensity. The corrected processed intensity may be corrected for non-saturable surface debris on the saturable absorber.

In various examples, the methods may include acquiring the first and second reflected intensities by employing one or more of: a two dimensional charge coupled device, a linear charge coupled device, a two dimensional complementary metal-oxide-semiconductor device, a linear complementary metal-oxide-semiconductor device, and a photomultiplier tube.

In some examples, the methods may include acquiring the first and second reflected intensities by one of: raster scanning, line scanning, staring array imaging, confocal imaging, and time-domain imaging. The saturable absorber may be substantially planar.

In various examples, the methods may include identifying the one or more defects at one or more locations on the saturable absorber where the reflected intensity ratio may be substantially equal to the incident intensity ratio. The methods may include employing a defect look-up-table to identify one or more defects at one or more of the plurality of locations on the saturable absorber.

In some examples, the methods may include inferring a location of a defect in a substrate from a location of a detected defect on the saturable absorber, wherein the saturable absorber may be located on a substrate. The saturable absorber may be graphene.

In several examples, the methods may include computing a processed intensity from the first and second reflected intensities according to the following formula:

$$I_{C.2} = I_B - (I_a/I_b)I_A$$

where: $I_{C.2}$ may represent the processed intensity; $I_A$ may represent the first reflected intensity; $I_B$ may represent the second reflected intensity; $I_a$ may represent a first baseline reflected intensity of the saturable absorber under bright field electromagnetic radiation at the first incident intensity; and $I_b$ may represent a second baseline reflected intensity of the saturable absorber under bright field electromagnetic radiation at the second incident intensity. The methods may also include acquiring a third reflected intensity of the saturable absorber for the location under dark field electromagnetic radiation at a third incident intensity; and computing a corrected processed intensity according to the following formula:

$$I_{C.2}'=I_C-I_D=I_B-(I_a/I_b)I_A-I_D$$

where: $I_C'$ may represent the corrected processed intensity; and $I_D$ may represent the third reflected intensity of the saturable absorber for the location under dark field electromagnetic radiation at the third incident intensity. The corrected processed intensity may be corrected for non-saturable surface debris on the saturable absorber.

In various examples, the substrate may include a metal, a semiconductor, a ceramic, or a polymer. The methods may include identifying the defect at one or more locations in the substrate where the reflected intensity ratio may be substantially equal to the incident intensity ratio.

In various examples, computer-readable storage media having machine executable instructions stored thereon for detecting defects may be provided. The computer readable storage media may include machine executable instructions to control an illumination source to selectively direct bright field electromagnetic radiation at a first incident intensity to a location on the saturable absorber at the sample stage. Instructions may be included to control an imaging device to acquire a first reflected intensity of the saturable absorber for the location under bright field electromagnetic radiation at the first incident intensity. Instructions may also be included to control the illumination source to selectively direct bright field electromagnetic radiation at a second incident intensity to the location on the saturable absorber. The second incident intensity may be greater than the first incident intensity by an amount sufficient to at least partly saturate an absorbance value of the saturable absorber. Instructions may be included to control the imaging device to acquire a second reflected intensity of the saturable absorber for the location under bright field electromagnetic radiation at the second incident intensity. Instructions may further be included to determine an incident intensity ratio corresponding to the second incident intensity divided by the first incident intensity. Instructions may be included to determine a reflected intensity ratio for the location corresponding to the second reflected intensity divided by the first reflected intensity. Instructions may also be included to generate a reflected intensity ratio map for the saturable absorber by determining reflected intensity ratios for a plurality of locations on the saturable absorber. The reflected intensity ratio map may be an image of one or more defects in the saturable absorber. Instructions may further be included to compare the reflected intensity ratio to the incident intensity ratio to identify one or more defects at one or more of the plurality of locations. Instructions may be included to identify an absence of defects at a location on the saturable absorber where the reflected intensity ratio may be greater than the incident intensity ratio.

In some examples, the computer readable storage media may include instructions to identify the one or more defects at one or more locations on the saturable absorber where the reflected intensity ratio may be substantially equal to the incident intensity ratio. The computer-readable storage may include a defect look-up-table. Instructions may be included to employ the defect look-up-table to identify one or more defects at one or more of the plurality of locations on the saturable absorber.

In several examples, the computer readable storage media may include instructions to control the illumination source to selectively direct dark field electromagnetic radiation at a third incident intensity to the location on the saturable absorber. Instructions may be included to control the imaging device to acquire a third reflected intensity of the saturable absorber for the location under dark field electromagnetic radiation at the third incident intensity. Instructions may also be included to compute a processed intensity and a corrected processed intensity from the first, second and third reflected intensities according to the following formulae:

$$I_C=I_A-(I_a/I_b)I_B$$

$$I_C'=I_C-I_D=I_A-(I_a/I_b)I_B-I_D$$

where: $I_C$ may represent the processed intensity; $I_A$ may represent the first reflected intensity; $I_B$ may represent the second reflected intensity; $I_a$ may represent a first baseline reflected intensity of the saturable absorber under bright field electromagnetic radiation at the first incident intensity; $I_b$ may represent a second baseline reflected intensity of the saturable absorber under bright field electromagnetic radiation at the second incident intensity; $I_C'$ may represent the corrected processed intensity. The corrected processed intensity may be corrected for non-saturable surface debris on the saturable absorber. $I_D$ may represent the third reflected intensity of the saturable absorber for the location under dark field electromagnetic radiation at the third incident intensity.

In various examples, the computer-readable storage media may further include machine executable instructions to: control the illumination source to selectively direct dark field electromagnetic radiation at a third incident intensity to the location on the saturable absorber at the sample stage; control the imaging device to acquire a third reflected intensity of the saturable absorber for the location under dark field electromagnetic radiation at the third incident intensity; and compute a processed intensity and a corrected processed intensity from the first, second and third reflected intensities according to the following formulae:

$$I_{C.2}=I_B-(I_a/I_b)\cdot I_A$$

$$I_{C.2}'=I_C-I_D=I_B-(I_a/I_b)I_A-I_D$$

where: $I_{C.2}$ may represent the processed intensity; $I_A$ may represent the first reflected intensity; $I_B$ may represent the second reflected intensity; $I_a$ may represent a first baseline reflected intensity of the saturable absorber under bright field electromagnetic radiation at the first incident intensity; $I_b$ may represent a second baseline reflected intensity of the saturable absorber under bright field electromagnetic radiation at the second incident intensity; $I_{C.2}'$ may represent the corrected processed intensity, wherein the corrected processed intensity may be corrected for non-saturable surface debris on the saturable absorber; and $I_D$ may represent the third reflected intensity of the saturable absorber for the location under dark field electromagnetic radiation at the third incident intensity.

Various example systems may be provided for detecting defects. The systems may include: a sample stage configured to hold a sample; an illumination source configured to selectively illuminate the sample stage under direct bright field and dark field electromagnetic radiation of selectable intensity; an imaging device configured to selectively acquire bright field reflected intensities and dark field reflected intensities of the sample; and a microprocessor coupled to the sample stage, the illumination source, and the imaging device. The microprocessor may be configured via machine executable instructions. Instructions may be included to control an illumination source to selectively direct bright field electromagnetic radiation at a first incident intensity to a location on the saturable absorber at the sample stage. Instructions may be included to control an imaging device to acquire a first reflected intensity of the saturable absorber for the location under bright field electromagnetic radiation at the first incident intensity. Instructions may also be included to control the illumination source to selectively direct bright field electromagnetic radiation at a second incident intensity to the location on the saturable absorber. The second incident intensity may be greater than the first incident intensity by an amount sufficient to at least partly saturate an absorbance value of the saturable absorber. Instructions may be included to control the imaging device to acquire a second reflected intensity of the saturable absorber for the location under bright field electromagnetic radiation at the second incident intensity. Instructions may further be included to determine an incident intensity ratio corresponding to the second incident intensity divided by the first incident intensity. Instructions may be included to determine a reflected intensity ratio for the location corresponding to the second reflected intensity divided by the first reflected intensity. Instructions may also be included to generate a reflected intensity ratio map for the saturable absorber by determining reflected intensity ratios for a plurality of locations on the saturable absorber. The reflected intensity ratio map may be an image of one or more defects in the saturable absorber. Instructions may further be included to compare the reflected intensity ratio to the incident intensity ratio to identify one or more defects at one or more of the plurality of locations. Instructions may be included to identify an absence of defects at a location on the saturable absorber where the reflected intensity ratio may be greater than the incident intensity ratio.

In several examples, instructions may be included to control the illumination source to selectively direct dark field electromagnetic radiation at a third incident intensity to the location on the saturable absorber. Instructions may be included to control the imaging device to acquire a third reflected intensity of the saturable absorber for the location under dark field electromagnetic radiation at the third incident intensity. Instructions may also be included to compute a processed intensity and a corrected processed intensity from the first, second and third reflected intensities according to the following formulae:

$$I_C = I_A - (I_a/I_b) I_B$$

$$I_C' = I_C - I_D = I_A - (I_a/I_b) I_B - I_D$$

where: $I_C$ may represent the processed intensity; $I_A$ may represent the first reflected intensity; $I_B$ may represent the second reflected intensity; $I_a$ may represent a first baseline reflected intensity of the saturable absorber under bright field electromagnetic radiation at the first incident intensity; $I_b$ may represent a second baseline reflected intensity of the saturable absorber under bright field electromagnetic radiation at the second incident intensity; $I_C'$ may represent the corrected processed intensity. The corrected processed intensity may be corrected for non-saturable surface debris on the saturable absorber. $I_D$ may represent the third reflected intensity of the saturable absorber for the location under dark field electromagnetic radiation at the third incident intensity.

In various examples, instructions may be included to control the illumination source to selectively direct dark field electromagnetic radiation at a third incident intensity to the location on the saturable absorber at the sample stage; control the imaging device to acquire a third reflected intensity of the saturable absorber for the location under dark field electromagnetic radiation at the third incident intensity; and compute a processed intensity and a corrected processed intensity from the first, second and third reflected intensities according to the following formulae:

$$I_{C.2} = I_B - (I_d/I_b) \cdot I_A$$

$$I_{C.2}' = I_C - I_D = I_B - (I_d/I_b) I_A - I_D$$

where: $I_{C.2}$ may represent the processed intensity; $I_A$ may represent the first reflected intensity; $I_B$ may represent the second reflected intensity; $I_a$ may represent a first baseline reflected intensity of the saturable absorber under bright field electromagnetic radiation at the first incident intensity; $I_b$ may represent a second baseline reflected intensity of the saturable absorber under bright field electromagnetic radiation at the second incident intensity; $I_{C.2}'$ may represent the corrected processed intensity, wherein the corrected processed intensity may be corrected for non-saturable surface debris on the saturable absorber; and $I_D$ may represent the third reflected intensity of the saturable absorber for the location under dark field electromagnetic radiation at the third incident intensity.

In various examples, the illumination source may include one of: a laser, a light emitting diode, a xenon lamp, and/or a microwave source. The imaging device may include one or more of: a two dimensional charge coupled device, a linear charge coupled device, a two dimensional complementary metal-oxide-semiconductor device, a linear complementary metal-oxide-semiconductor device, and/or a photomultiplier tube.

In several examples, the system may further include a sample manipulator operatively coupled to the microprocessor and configured to place the saturable absorber on a substrate. The microprocessor may be further configured via the machine executable instructions to control the sample manipulator to manipulate the saturable absorber.

In some examples, the system may further include a heater operatively coupled to the microprocessor and the sample stage, wherein the microprocessor may be further configured via the machine executable instructions to control the heater to heat the saturable absorber at the sample stage.

The terms "a" and "an" as used herein mean "one or more" unless the singular is expressly specified. For example, reference to "a base" may include a mixture of two or more bases, as well as a single base.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to, plus or minus 10% of the particular term.

As used herein, "substantially" will be understood by persons of ordinary skill in the art and will vary to some extent depending upon the context in which it is used. If there are uses of the term which are not clear to persons of ordinary skill in the art, given the context in which it is used, "about" will mean up to, plus or minus 10% of the particular term. For example, values which are "substantially equal" may be the same within up to plus or minus 10% of the value.

As used herein, the terms "optional" and "optionally" mean that the subsequently described circumstance may or may not occur, so that the description includes instances where the circumstance occurs and instances where it does not.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

A typical imaging system may be implemented utilizing any suitable commercially available components, such as those typically found in data computing/communication and/or network computing/communication systems. The herein described subject matter sometimes illustrates different components contained within, or coupled together with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

The various aspects and embodiments disclosed herein are for purposes of illustration and are not intended to be limiting, with the true scope and spirit being indicated by the following claims.

What is claimed is:

1. A method to detect one or more defects in a sample using a saturable absorber, comprising:
   acquiring a first reflected intensity of the saturable absorber for a location on the saturable absorber under a bright field electromagnetic radiation at a first incident intensity, wherein the first reflected intensity corresponds to one or more portions of a first reflected intensity image of the saturable absorber, and wherein the one or more portions of the first reflected intensity image exclude the one or more defects;
   acquiring a second reflected intensity of the saturable absorber for the location under the bright field electromagnetic radiation at a second incident intensity, the second incident intensity being greater than the first incident intensity by an amount sufficient to at least partly saturate an absorbance value of the saturable absorber, wherein the second reflected intensity corresponds to one or more portions of a second reflected intensity image of the saturable absorber, and wherein the one or more portions of the second reflected intensity image exclude the one or more defects;
   determining an incident intensity ratio that corresponds to the second incident intensity divided by the first incident intensity;
   determining a reflected intensity ratio for the location that corresponds to the second reflected intensity image divided by the first reflected intensity image;
   comparing the reflected intensity ratio to the incident intensity ratio to identify the one or more defects at the location; and
   distinguishing between the one or more defects based on the first reflected intensity at the location and the second reflected intensity at the location, wherein the first reflected intensity is identified as a lower reflectivity due to an association with gaps in the saturable absorber, and wherein the second reflected intensity is identified as a greater reflectivity due to a non-linear absorption of the saturable absorber.

2. The method of claim 1, further comprising identifying an absence of the one or more defects at the location on the saturable absorber where the reflected intensity ratio is greater than the incident intensity ratio.

3. The method of claim 1, wherein the saturable absorber includes one or more of: graphene, carbon nanotubes, a semiconductor, and a metal.

4. The method of claim 1, wherein the incident intensity ratio is from about 2:1 to about 200:1.

5. The method of claim 1, wherein the first incident intensity the second incident intensity of the electromagnetic radiation have an average value from about 0.1 Watts per square centimeter to about 500 Watts per square centimeter.

6. The method of claim 1, wherein the first incident intensity and the second incident intensity of the electromagnetic radiation have an average value from about 0.1 Watts per square centimeter to about 500 Watts per square centimeter.

7. The method of claim 1, wherein the electromagnetic radiation has a wavelength from about 150 nanometers to about 1 micrometer.

8. The method of claim 1, further comprising computing a processed intensity from the first reflected intensity and the second reflected intensity according to a formula:

$$I_C = I_A - (I_a/I_b)I_B$$

wherein:
   $I_C$ represents the processed intensity;
   $I_A$ represents the first reflected intensity;
   $I_B$ represents the second reflected intensity;
   $I_a$ represents a first baseline reflected intensity of the saturable absorber under the bright field electromagnetic radiation at the first incident intensity; and $I_b$ represents a second baseline reflected intensity of the saturable absorber under the bright field electromagnetic radiation at the second incident intensity.

9. The method of claim 8, further comprising:

acquiring a third reflected intensity of the saturable absorber for the location under dark field electromagnetic radiation at a third incident intensity; and computing a corrected processed intensity according to a formula:

$$I_C'=I_C-I_D=I_A-(I_a/I_b)\cdot I_B-I_D$$

wherein:

$I_C'$ represents the corrected processed intensity; and $I_D$ represents the third reflected intensity of the saturable absorber for the location under the dark field electromagnetic radiation at the third incident intensity, wherein the corrected processed intensity is corrected for non-saturable surface debris on the saturable absorber.

10. The method of claim 1, wherein acquiring the first reflected intensity and acquiring the second reflected intensity respectively include acquiring the first reflected intensity and the second reflected intensity by one of: raster scanning, line scanning, staring array imaging, confocal imaging, and time-domain imaging.

11. The method of claim 1, wherein the saturable absorber is substantially planar.

12. The method of claim 1, further comprising employing a defect look-up-table to identify the one or more defects at the location on the saturable absorber.

13. The method of claim 12, further comprising computing a processed intensity from the first reflected intensity and the second reflected intensity according to a formula:

$$I_{C,2}=I_B-(I_a/I_b)I_A$$

wherein:

$I_{C,2}$ represents the processed intensity;

$I_A$ represents the first reflected intensity;

$I_B$ represents the second reflected intensity;

$I_a$ represents a first baseline reflected intensity of the saturable absorber under the bright field electromagnetic radiation at the first incident intensity; and $I_b$ represents a second baseline reflected intensity of the saturable absorber under the bright field electromagnetic radiation at the second incident intensity.

14. The method of claim 13, further comprising:

acquiring a third reflected intensity of the saturable absorber for the location under dark field electromagnetic radiation at a third incident intensity; and computing a corrected processed intensity according to a formula:

$$I_{C,2}'=I_C-I_D=I_B-(I_a/I_b)\cdot I_A-I_D$$

wherein:

$I_C'$ represents the corrected processed intensity; and $I_D$ represents the third reflected intensity of the saturable absorber for the location under the dark field electromagnetic radiation at the third incident intensity, wherein the corrected processed intensity is corrected for non-saturable surface debris on the saturable absorber.

15. The method of claim 1, further comprising:

inferring a location of the one or more defects in a substrate from a location of the one or more defects on the saturable absorber, wherein the saturable absorber is located on the substrate.

16. The method of claim 15, wherein the substrate includes one or more of: a metal, a semiconductor, a ceramic, and a polymer.

17. The method of claim 15, further comprising identifying the one or more defects at the location in the substrate where the reflected intensity ratio is substantially equal to the incident intensity ratio.

18. A non-transitory computer-readable storage medium having machine executable instructions stored thereon to detect one or more defects in a sample using a saturable absorber, comprising machine executable instructions to:

control an illumination source to direct a bright field electromagnetic radiation at a first incident intensity to a location on the saturable absorber at a sample stage;

control an imager device to acquire a first reflected intensity of the saturable absorber for the location under the bright field electromagnetic radiation at the first incident intensity, wherein the first reflected intensity corresponds to one or more portions of a first reflected intensity image of the saturable absorber, and wherein the one or more portions of the first reflected intensity image exclude the one or more defects;

control the illumination source to direct the bright field electromagnetic radiation at a second incident intensity to the location on the saturable absorber, the second incident intensity being greater than the first incident intensity by an amount sufficient to at least partly saturate an absorbance value of the saturable absorber;

control the imager device to acquire a second reflected intensity of the saturable absorber for the location under bright field electromagnetic radiation at the second incident intensity, wherein the second reflected intensity corresponds to one or more portions of a second reflected intensity image of the saturable absorber, and wherein the one or more portions of the second reflected intensity image exclude the one or more defects;

determine an incident intensity ratio that corresponds to the second incident intensity divided by the first incident intensity;

determine a reflected intensity ratio for the location that corresponds to the second reflected intensity image divided by the first reflected intensity image;

compare the reflected intensity ratio to the incident intensity ratio to identify the one or more defects at the plurality of the location;

distinguish between the one or more defects based on the first reflected intensity at the location and the second reflected intensity at the location, wherein the first reflected intensity is identified as a lower reflectivity due to an association with gaps in the saturable absorber, and wherein the second reflected intensity is identified as a greater reflectivity due to a non-linear absorption of the saturable absorber; and identify an absence of the one or more defects at the location on the saturable absorber where the reflected intensity ratio is greater than the incident intensity ratio.

19. The non-transitory computer-readable storage medium of claim 18, further comprising machine executable instructions to identify the one or more defects at the location on the saturable absorber where the reflected intensity ratio is substantially equal to the incident intensity ratio.

20. The non-transitory computer-readable storage medium of claim 18, further comprising machine executable instructions to incorporate the one or more defects into a defect look-up-table.

21. The non-transitory computer-readable storage medium of claim 18, further comprising machine executable instructions to:
control the illumination source to direct dark field electromagnetic radiation at a third incident intensity to the location on the saturable absorber;
control the imager device to acquire a third reflected intensity of the saturable absorber for the location under the dark field electromagnetic radiation at the third incident intensity;
compute a processed intensity and a corrected processed intensity from the first, second and third reflected intensities according to a formula:

$$I_C = I_A - (I_a/I_b)I_B$$

$$I_C' = I_C - I_D = I_A - (I_a/I_b)I_B - I_D$$

wherein:
$I_C$ represents the processed intensity;
$I_A$ represents the first reflected intensity;
$I_B$ represents the second reflected intensity;
$I_a$ represents a first baseline reflected intensity of the saturable absorber under bright field electromagnetic radiation at the first incident intensity;
$I_b$ represents a second baseline reflected intensity of the saturable absorber under the bright field electromagnetic radiation at the second incident intensity;
$I_C'$ represents the corrected processed intensity, wherein the corrected processed intensity is corrected for non-saturable surface debris on the saturable absorber; and
$I_D$ represents the third reflected intensity of the saturable absorber for the location under the dark field electromagnetic radiation at the third incident intensity.

22. The non-transitory computer-readable storage medium of claim 18, further comprising machine executable instructions to:
control the illumination source to direct dark field electromagnetic radiation at a third incident intensity to the location on the saturable absorber at the sample stage;
control the imager device to acquire a third reflected intensity of the saturable absorber for the location under the dark field electromagnetic radiation at the third incident intensity;
compute a processed intensity and a corrected processed intensity from the first, second and third reflected intensities according to a formula:

$$I_{C.2} = I_B - (I_a/I_b) \cdot I_A$$

$$I_{C.2}' = I_C - I_D = I_B - (I_a/I_b)I_A - I_D$$

wherein:
$I_{C.2}$ represents the processed intensity;
$I_A$ represents the first reflected intensity;
$I_B$ represents the second reflected intensity;
$I_a$ represents a first baseline reflected intensity of the saturable absorber under bright field electromagnetic radiation at the first incident intensity;
$I_b$ represents a second baseline reflected intensity of the saturable absorber under bright field electromagnetic radiation at the second incident intensity;
$I_{C.2}'$ represents the corrected processed intensity, wherein the corrected processed intensity is corrected for non-saturable surface debris on the saturable absorber; and
$I_D$ represents the third reflected intensity of the saturable absorber for the location under the dark field electromagnetic radiation at the third incident intensity.

23. A system to detect one or more defects, the system comprising:
a sample stage configured to hold a sample;
an illumination source configured to illuminate the sample stage under direct bright field and dark field electromagnetic radiation of selectable intensity;
an imager device configured to acquire bright field reflected intensities and dark field reflected intensities of the sample;
a microprocessor coupled to the sample stage, the illumination source, and the imager device, wherein the microprocessor is configured via machine executable instructions to:
control the illumination source to direct bright field electromagnetic radiation at a first incident intensity to a location on a saturable absorber at the sample stage;
control the imager device to acquire a first reflected intensity of the saturable absorber for the location under bright field electromagnetic radiation at the first incident intensity, wherein the first reflected intensity corresponds to one or more portions of a first reflected intensity image of the saturable absorber, and wherein the one or more portions of the first reflected intensity image exclude the one or more defects;
control the illumination source to direct the bright field electromagnetic radiation at a second incident intensity to the location on the saturable absorber at the sample stage, the second incident intensity being greater than the first incident intensity by an amount sufficient to at least partly saturate an absorbance value of the saturable absorber;
control the imager device to acquire a second reflected intensity of the saturable absorber for the location under bright field electromagnetic radiation at the second incident intensity, wherein the second reflected intensity corresponds to one or more portions of a second reflected intensity image of the saturable absorber, and wherein the one or more portions of the second reflected intensity image exclude the one or more defects;
determine an incident intensity ratio that corresponds to the second incident intensity divided by the first incident intensity;
determine a reflected intensity ratio for the location that corresponds to the second reflected intensity image divided by the first reflected intensity image;
compare the reflected intensity ratio to the incident intensity ratio to identify the one or more defects at the location;
distinguish between the one or more defects based on the first reflected intensity of the location and the second reflected intensity of the location, wherein the first reflected intensity is identified as a lower reflectivity due to an association with gaps in the saturable absorber, and wherein the second reflected intensity is identified as a greater reflectivity due to a non-linear absorption of the saturable absorber; and
identify an absence of the one or more defects at the location on the saturable absorber where the reflected intensity ratio is greater than the incident intensity ratio.

24. The system of claim 23, wherein the illumination source includes one of: a laser, a light emitting diode, a xenon lamp, and a microwave source.

25. The system of claim 23, wherein the imager device includes one or more of: a two dimensional charge coupled device, a linear charge coupled device, a two dimensional complementary metal-oxide-semiconductor device, a linear complementary metal-oxide-semiconductor device, and a photomultiplier tube.

26. The system of claim 23, further comprising a sample manipulator operatively coupled to the microprocessor and configured to place the saturable absorber on a substrate, wherein the microprocessor is further configured via the machine executable instructions to control the sample manipulator to manipulate the saturable absorber.

27. The system of claim 23, further comprising a heater operatively coupled to the microprocessor and the sample stage, wherein the microprocessor is further configured via the machine executable instructions to control the heater to heat the saturable absorber at the sample stage.

* * * * *

UNITED STATES PATENT AND TRADEMARK OFFICE
CERTIFICATE OF CORRECTION

| | |
|---|---|
| PATENT NO. | : 9,103,803 B2 |
| APPLICATION NO. | : 13/825492 |
| DATED | : August 11, 2015 |
| INVENTOR(S) | : Yager |

It is certified that error appears in the above-identified patent and that said Letters Patent is hereby corrected as shown below:

In Column 1, Line 8, delete "§371" and insert -- § 371 --, therefor.

In Column 27, Line 54, in Claim 14, in Equation, delete "$I_{C.2}=I_C-I_D=I_B-(I_a/I_b)\cdot I_A-I_D$" and insert -- $I_{C.2}' = I_C - I_D = I_B - (I_a/I_b)\bullet I_A - I_D$ --, therefor.

In Column 28, Lines 46-47, in Claim 18, delete "plurality of the".

Signed and Sealed this
Twenty-ninth Day of March, 2016

Michelle K. Lee
*Director of the United States Patent and Trademark Office*